United States Patent
Liu et al.

(10) Patent No.: US 11,147,853 B2
(45) Date of Patent: Oct. 19, 2021

(54) POLYPEPTIDE BINDING TO A PLURALITY OF AMYLOID MONOMERS AND AGGREGATES, AND USE THEREOF

(71) Applicant: Hangzhou Wisdom Panacea Biologics Co., Ltd., Hangzhou (CN)

(72) Inventors: Ruitian Liu, Beijing (CN); Xiaolin Yu, Beijing (CN)

(73) Assignee: Hangzhou Wisdom Panacea Biologics Co., Ltd.

( * ) Notice: Subject to any disclaimer, the term of this patent is extended or adjusted under 35 U.S.C. 154(b) by 127 days.

(21) Appl. No.: 15/778,324

(22) PCT Filed: Nov. 21, 2016

(86) PCT No.: PCT/CN2016/106585
§ 371 (c)(1),
(2) Date: Sep. 19, 2018

(87) PCT Pub. No.: WO2017/088711
PCT Pub. Date: Jun. 1, 2017

(65) Prior Publication Data
US 2019/0330271 A1    Oct. 31, 2019

(30) Foreign Application Priority Data
Nov. 25, 2015  (CN) .......................... 201510831563.X

(51) Int. Cl.
| | |
|---|---|
| *A61K 38/08* | (2019.01) |
| *C07K 7/06* | (2006.01) |
| *A61P 25/28* | (2006.01) |
| *C12N 15/11* | (2006.01) |
| *C12N 15/63* | (2006.01) |
| *A61K 38/00* | (2006.01) |

(52) U.S. Cl.
CPC .............. *A61K 38/08* (2013.01); *A61P 25/28* (2018.01); *C07K 7/06* (2013.01); *C12N 15/11* (2013.01); *C12N 15/63* (2013.01); *A61K 38/00* (2013.01)

(58) Field of Classification Search
CPC ......... A61K 38/00; A61K 38/08; A61P 25/28; C07K 7/06; C12N 15/11; C12N 15/63
See application file for complete search history.

(56) References Cited

U.S. PATENT DOCUMENTS

| | | | | |
|---|---|---|---|---|
| 9,605,040 | B2 * | 3/2017 | von Maltzahn | ....... A23L 33/175 |
| 9,932,560 | B2 * | 4/2018 | Ko | ....................... C12N 5/0696 |
| 2013/0053320 | A1 * | 2/2013 | Gozes | ................... A23C 9/1526 |
| | | | | 514/13.5 |

FOREIGN PATENT DOCUMENTS

| | | |
|---|---|---|
| CN | 101263154 A | 9/2008 |
| CN | 102060911 A | 5/2011 |
| JP | 2008530194 | 8/2008 |
| WO | 2011144714 A1 | 11/2011 |
| WO | 2011156003 A2 | 12/2011 |

OTHER PUBLICATIONS

Berg JM, Tymoczko JL, Stryer L. Biochemistry. 5th edition. New York: W H Freeman; 2002 5 pages (Year: 2002).*
Zhang, et al. "Research on the Biological Characteristics of Intramembranous Fragments of Amyloid-ß Related with AD," Progress in Modem Biomedicine, (2012). vol. 12, No. 21, pp. 4023-4026.
Kayed, et al. "Common Structure of Soluble Amyloid Oligomers Implies Common Mechanism of Pathogensis," Science, (2003). vol. 300, pp. 486-486.
Balbach, et al. "Amyloid Fibril Formation by Aß16-22, a Seven-Residue Fragment of the Alzheimer's ß-Amyloid Peptide, and Structural Characterization by Solid State NMR," Biochemistry, (2000). vol. 39, No. 45, pp. 13748-13759.
International Search Report dated Feb. 4, 2017; International Patent Application No. PCT/CN2016/106585 filed Nov. 21, 2016. ISR/CN.
European Office Action (EPO), Communication Pursuant to Rule 164(1) EPC for Application No. 16867934.8, dated May 10, 2019, 12 pages, European Patent Office, Germany.
Ashur-Fabian, O. et al., "The Neuroprotective Peptide Nap Inhibits the Aggregation of the Beta-Amyloid Peptide." Elsevier Inc.. 2003, pp. 1413-1423.

(Continued)

Primary Examiner — Thomas S Heard
(74) Attorney, Agent, or Firm — McDonald Hopkins LLC

(57) ABSTRACT

Disclosed is a polypeptide binding to a plurality of amyloid monomers and aggregates, characterised in that: the polypeptide contains the amino acid sequences as shown in (a) and/or (b): (a) the general formula of the amino acid sequence is Ser-$X_1$-Phe-$X_2$-Asn-Lys-Arg, wherein $X_1$ and $X_2$ are independently any one of the 20 amino acids; and (b) the variant having the function of the polypeptide and modifying the general formula (a) of the amino acid sequence by the substitution, deletion or addition of one or more amino acid residues. The polypeptide with a small molecular weight can specifically bind to the oligomers of Aβ42, amylin, insulin and lysozyme and the monomers of Aβ42 and amylin, as well as fibres, can inhibit the aggregation of Aβ42 and lysozyme and inhibit the cytotoxicity of Aβ42, amylin, insulin and lysozyme, and can protect the nerve cells from the influence of Aβ42 toxicity, so that same has a wide application prospect in the prevention and treatment of diseases of amyloids like AD, PD, HD, T2DM, etc.

12 Claims, 31 Drawing Sheets
Specification includes a Sequence Listing.

(56) References Cited

OTHER PUBLICATIONS

Findeis, M., "Peptide Inhibitors of Beta Amyloid Aggregation." Current Topics in Medicinal Chemistry. 2002. vol. 2, No. 4, pp. 417-423.
Extended European Search Report dated Aug. 13, 2019. European Patent Application No. 16867934.8.
Larsson Par et al: "The complete genome 1,2,4-11sequence of *Francisella tularensis*, the causative agent of tularemia", Nature Genetics, Nature Publishing Group, New York, US, vol. 37, No. 2, Feb. 1, 2005 (Feb. 1, 20051), pp. 153-159, XP002421763, (Feb. 27, 2015).
A. Khamis et al: "rpoB Gene Sequencing for Identification of *Corynebacterium* Species", Journal of Clinical Microbiology, vol. 42, No. 9, Sep. 1, 2004 (Sep. 1, 2004), pp. 3925-3931, XP055609453, (Sep. 14, 2004).
XP-002793254.
XP-002793255.

* cited by examiner

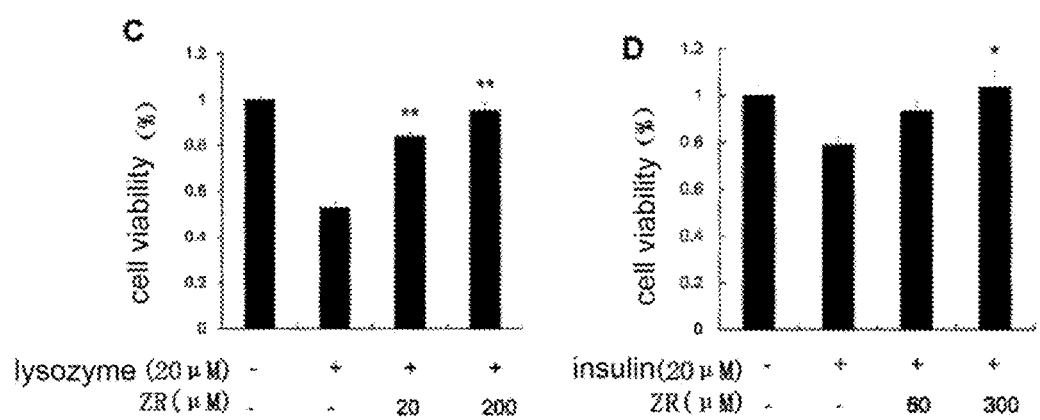
FIG.5C  FIG.5D

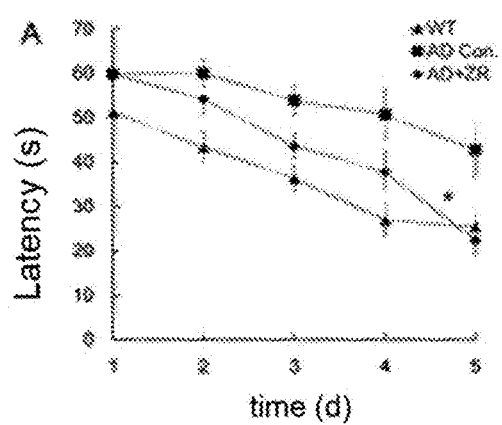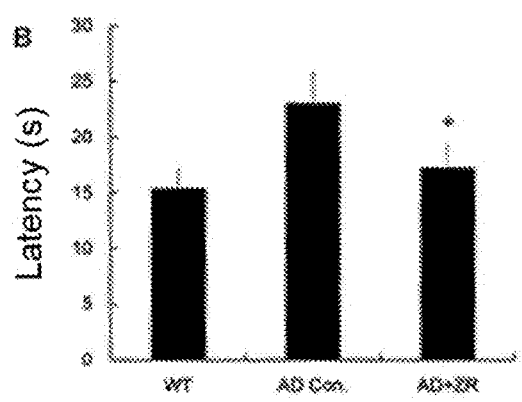
FIG.6A　　　　　　　　FIG.6B

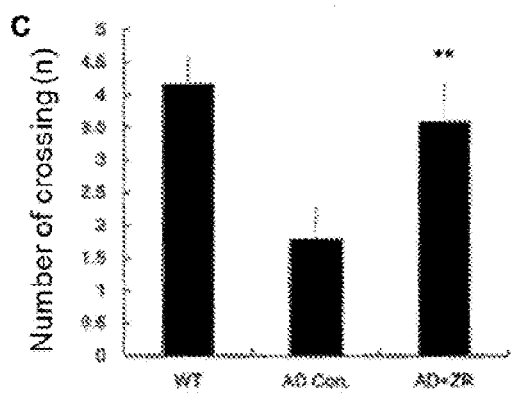 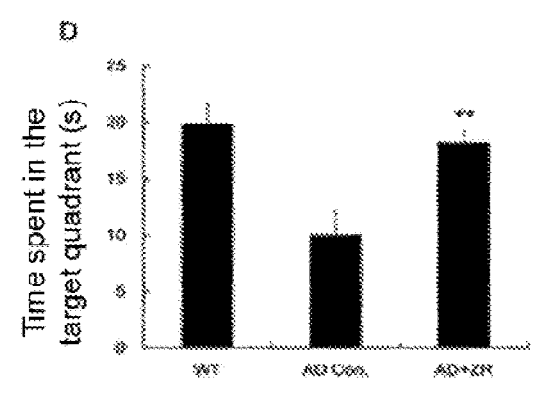
FIG.6C　　　　　　FIG.6D

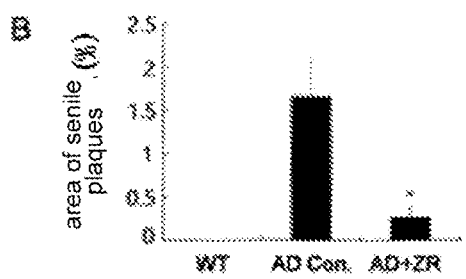
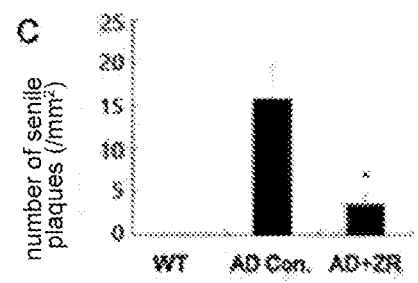
FIG.7B          FIG.7C

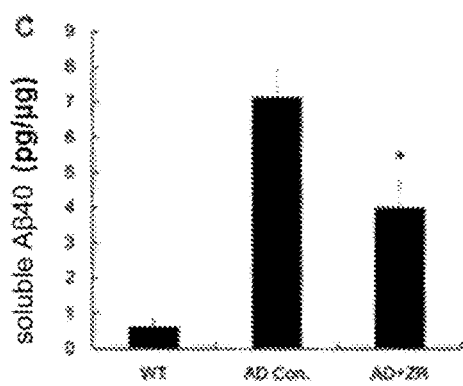 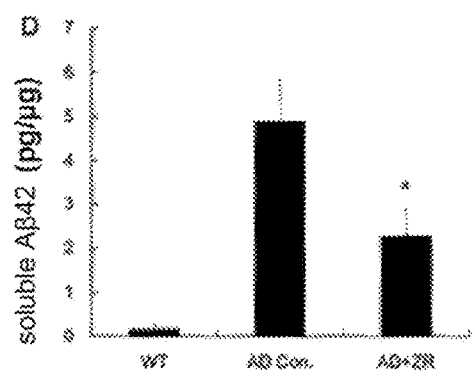
FIG.8C     FIG.8D

POLYPEPTIDE BINDING TO A PLURALITY OF AMYLOID MONOMERS AND AGGREGATES, AND USE THEREOF

CROSS-REFERENCE TO RELATED APPLICATION

This application is a 35 U.S.C. 371 national stage filing of PCT Application No. PCT/CN2016/106585 filed on Nov. 21, 2016, which claims priority to Chinese Patent Application No. 201510831563.X, filed on Nov. 25, 2015, each of which are incorporated herein in their entirety by reference.

REFERENCE TO SEQUENCE LISTING SUBMITTED ELECTRONICALLY VIA EFS-WEB

The content of the electronically submitted sequence listing (Name: 129SequenceListing.txt; Size: 2696 bytes; and Date of Creation: Jul. 4, 2019) is herein incorporated by reference in its entirety.

TECHNICAL FIELD

The present invention relates to the field of biotechnology, in particular to a polypeptide, and even in particular to a polypeptide binding to a plurality of amyloid monomers and aggregates and application thereof.

BACKGROUND

Amyloid disease is a collective term for more than twenty diseases caused by the aggregation of amyloid, including Alzheimer's disease (AD), commonly known as senile dementia, Parkinson' disease (PD), Huntington's disease (HD), and etc. Different amyloid diseases have different lesion sites, mainly involving the nervous system, heart, liver, kidneys, and etc. The monomers of some proteins have no toxicity or little toxicity by themselves, and however, they can aggregate into oligomers or fibrils with toxicity, thereby resulting in a series of diseases. For example, β-amyloid (Aβ) can result in AD; α-synuclein can result in PD; prion protein (PrP) can result in at least more than 10 kinds of brain diseases in human and animal, including mad cow disease; a polypeptide containing polyglutamine (PolyQ) can result in at least 9 kinds of hereditary neurodegenerative diseases including HD; and islet amyloid polypeptide (IAPP, amylin) can result in type II diabetes and diseases caused by aggregation and deposition of lysozyme due to prolonged dialysis. Among them, AD, PD and type II diabetes do the greatest harm to human health. Medical statistics show that 5-6% of elderly persons over 65 years of age in China and European and American countries suffer from AD, and the incidence rate increases year by year. This disease has been ranked as the fourth leading cause of death, second only to heart disease, cancer and stroke. About 1% of elderly persons over 65 years of age suffer from PD. Moreover, the number of people suffering from type II diabetes accounts for more than 5% of the total population. These diseases do great harm to human health. The underlying causes (or part thereof) of these diseases lie in the aggregation of certain proteins by themselves.

Studies have shown that the aggregation of various proteins initially begins with misfolded or denatured protein monomers, and the formation of hydrogen bonds between polypeptide chains of the monomers results in the aggregation of the protein molecules. Soluble spherical oligomers having a size of about 3-10 nm which can be observed by electronic force or atomic force microscope are first formed. Some oligomers can further aggregate into curved and flexible protofibrils, which in turn form fibers having a diameter of 6-10 nm with smooth surface or in spiral shape. Non-homologous proteins can eventually form protein polymers with similar structures. All fibers formed by the aggregation of various proteins such as Aβ, α-synuclein, PrP, IAPP, insulin and lysozyme contain a "cross-Beta" structure, in which the backbone constituted by β-sheet is perpendicular to the longitudinal axis of the fiber, while the hydrogen bond network in the backbone is parallel to the longitudinal axis. The polypeptides are arranged as parallel β-strands in the β-sheet and amino acids have precise positions in the β-sheet. Oligomers derived from different sources also have similar structural characteristics, and the oligomer-specific antibodies can bind to oligomers formed by protein monomers derived from different sources, but not bind to their monomers and fibers, indicating that the amyloidogenic proteins can form a general antigen epitope specific to oligomers independent of their amino acid sequence. Antibody (A11) which can not only bind to Aβ40 and Aβ42 oligomers but also bind to oligomers formed by α-synuclein, IAPP, PolyQ, PrP, insulin, lysozyme, etc, has been prepared by Glabe's lab by using gold colloid particles linked with Aβ40 to imitate Aβ40 oligomers, and this antibody can also effectively inhibit the cytotoxicity of all these oligomers.

In the past, it has been thought that the occurrence of amyloid diseases is caused by insoluble fibrous substances formed by the aggregation of proteins. In recent years, a large number of studies have shown that the key factor causing diseases is soluble oligomers. The neurodegenerative diseases caused by amyloid oligomers involve similar cytotoxic mechanisms, i.e., cell membrane damage, oxidative stress, mitochondrial dysfunction, abnormal signal transmission, cell apoptosis. The mechanism of oligomer formation and how to effectively inhibit its cytotoxicity need to be investigated and solved urgently. As for Aβ, it can form different forms of oligomers, such as fibrillar oligomers (FO), prefibrillar oligomers (PFO). The former can further aggregate to form fibers, while the latter cannot. FO and PFO can be recognized by the conformation-dependent antibodies OC and A11, respectively. Aβ can also form other forms of oligomers, such as oligomers that can be recognized by single-chain antibody W20, but not by OC or A11. Studies have shown that these three types of antibodies can not only bind to Aβ, but also bind to oligomers of other amyloids such as α-synuclein, amylin, insulin and lysozyme, indicating that multiple amyloid oligomers have the same structure features independent of proteins and sequences. Similarly, fibers formed by the aggregation of various amyloids can also have a common steric structure and bind to the same antibody. However, it has not been reported whether there is an identical structure independent of the protein primary sequence between the monomers, oligomers, and fibers of various amyloids.

AD is a progressive neurodegenerative disease, which is characterized by progressive loss of memory and formation of senile plaques by Aβ aggregation in brain. Aβ oligomers can accumulate at synapses, causing synaptic degeneration and hyperphosphorylation of tau protein. Currently, the treatment strategies for amyloidosis generally include: inhibiting the production, aggregation or cytotoxicity of amyloidogenic proteins and promoting their clearance. Moreover, the occurrence and development of diseases caused by amyloids are also related to oxidative stress, production of nitric oxide, and generation of inflammatory factors caused by the same.

Therefore, successful drugs for treating amyloid diseases should be multifunctional. Peptide drugs, which have been widely concerned by the medical community for more than a decade, have the advantage of low immunogenicity, low toxicity, and their specificity, stability, and penetrability which can be easily increased by biotechnological methods. CN 104277105 A discloses a polypeptide that inhibits the aggregation and toxicity of β-amyloid, or variants thereof which maintain the function of said polypeptide. The polypeptide of the invention has ability of binding to Aβ protein, which can greatly reduce the effective content of β-sheet structure when the aggregation of Aβ reaches an equilibrium state, and can change the secondary structure of Aβ in solution environment, so that the content of β-sheet structure is greatly reduced or even disappeared. In addition, the polypeptide can significantly reduce the toxicity of Aβ on SH-SY5Y cells and can greatly inhibit the production of reactive oxygen species induced by Aβ even at a very low concentration, thereby providing a feasible method for the treatment of AD. However, the polypeptide in the invention can only specifically recognize and bind to Aβ monomers, inhibit Aβ aggregation, cytotoxicity, oxidative stress and neuroinflammation, and the like, but cannot simultaneously recognize multiple amyloid monomers, oligomers and fibers.

SUMMARY OF THE INVENTION

It is an object of the present invention to provide a polypeptide and application thereof, and in particular a polypeptide binding to a plurality of amyloid monomers and aggregates and application thereof. The polypeptide can not only bind to Aβ protein, but also bind to other amyloids including amylin, insulin lysozyme, and etc.

In order to achieve the object of the invention, the present invention adopts the following technical solutions:

In a first aspect, the present invention provides a polypeptide binding to a plurality of amyloid monomers and aggregates, wherein said polypeptide comprises the amino acid sequences shown in (a) and/or (b):

(a) the amino acid sequence having a general formula of: Ser-$X_1$-Phe-$X_2$-Asn-Lys-Arg, wherein $X_1$ and $X_2$ are independently any one of the 20 amino acids;

(b) a variant obtained by modifying the general formula of the amino acid sequence (a) through substitution, deletion or addition of one or more amino acids, which maintains the function of said polypeptide.

In the present invention, the polypeptide has a low molecular weight, can specifically bind to oligomers of Aβ42, amylin, insulin and lysozyme, and monomers and fibers of Aβ42 and amylin, can inhibit the aggregation of Aβ42 and lysozyme, can inhibit the cytotoxicity of Aβ42, amylin, insulin and lysozyme, and can protect neuronal cells from Aβ42 toxicity.

Preferably, the polypeptide has an amino acid sequence as shown in SEQ ID NOs. 1-2, or is a variant obtained by modifying the amino acid sequence as shown in SEQ ID NOs. 1-2 through substitution, deletion or addition of one or more amino acid residues, which maintains the function of said polypeptide.

Preferably, the sequence of the variant is selected from, but not limited to the emphatically listed SEQ ID Nos. 3-6.

The amino acid sequences are as follows:

SEQ ID NO. 1: Ser-$X_1$-Phe-$X_2$-Asn-Lys-Arg;

SEQ ID NO. 2: Ser-Phe-Phe-Asn-Asn-Lys-Arg;

(ZR Polypeptide)

SEQ ID NO. 3: Ser-Phe-Phe-Asn-Lys-Arg;

SEQ ID NO. 4: Ser-Ala-Phe-Gln-Asn-Lys-Arg;

SEQ ID NO. 5: Ser-Phe-Phe-Asn-Asn-Asn-Lys-Arg;

SEQ ID NO. 6: Ser-Phe-Phe-Asn-Asn-Lys-Arg-Lys.

In a second aspect, the present invention provides a DNA fragment, comprising a nucleotide sequence encoding the polypeptide according to the first aspect.

In a third aspect, the present invention provides a recombinant vector, comprising at least one copy of the DNA fragment according to the second aspect.

In a fourth aspect, the present invention provides a recombinant cell, comprising the recombinant vector according to the third aspect.

In a fifth aspect, the present invention provides an inhibitor of amyloid cytotoxicity, comprising any one of the polypeptide according to the first aspect, the DNA fragment according to the second aspect, the recombinant vector according to the third aspect, or the recombinant cell according to the fourth aspect, or a combination of at least two thereof.

Preferably, the inhibitor is useful for inhibiting the cytotoxicity of Aβ, amylin, insulin and lysozyme on cells.

Preferably, the cells are SH-SY5Y neuroblastoma cells.

In a sixth aspect, the present invention provides an inhibitor of amyloid aggregation, comprising any one of the polypeptide according to the first aspect, the DNA fragment according to the second aspect, the recombinant vector according to the third aspect, or the recombinant cell according to the fourth aspect, or a combination of at least two thereof.

Preferably, the inhibitor is useful for inhibiting the aggregation of Aβ and lysozyme.

In a seventh aspect, the present invention provides a promoter for the clearance of Aβ by cells, comprising any one of the polypeptide according to the first aspect, the DNA fragment according to the second aspect, the recombinant vector according to the third aspect, or the recombinant cell according to the fourth aspect, or a combination of at least two thereof.

Preferably, the cells are microglia cells, preferably BV-2 cells.

Preferably, the Aβ is Aβ42.

In the present invention, the promoter for the clearance of Aβ can increase the phagocytosis of Aβ by microglia cells.

In an eighth aspect, the present invention provides a pharmaceutical composition, comprising any one of the polypeptide according to the first aspect, the DNA fragment according to the second aspect, the recombinant vector according to the third aspect, or the recombinant cell according to the fourth aspect, or a combination of at least two thereof.

Preferably, the pharmaceutical composition further comprises a pharmaceutically acceptable adjuvant.

Preferably, the adjuvant is any one of an excipient, a diluent, a carrier, a flavoring agent, a binder and a filler, or a combination of at least two thereof.

Preferably, the pharmaceutical composition is useful in the manufacture of a medicament for detecting, diagnosing and/or treating amyloid-related diseases.

Preferably, the diseases include any one of Alzheimer's disease (AD), Parkinson's disease (PD), Huntington's disease (HD), or type II diabetes (T2DM), or a combination of at least two thereof.

In the present invention, the polypeptide can improve the spatial memory of AD transgenic mice, reduce the number of senile plaques in the brain of mice, and/or reduce the levels of Aβ40 and Aβ42 and the inflammatory response in the brain of mice; the polypeptide can improve the motor coordination of PD transgenic mice and reduce α-synuclein level in the brain of PD transgenic mice; the polypeptide can also improve the motor coordination of HD transgenic mice and reduce the mutant HTT protein level in the brain of HD transgenic mice.

Compared with the prior art, the present invention has the following beneficial effects:

(1) The polypeptide of the present invention has a low molecular weight and can specifically bind to oligomers of Aβ42, amylin, insulin and lysozyme, and to monomers and fibers of Aβ42 and amylin, can inhibit the aggregation of Aβ42 and lysozyme, and inhibit the cytotoxicity of Aβ42, amylin, insulin and lysozyme, and can protect neuronal cells from Aβ42-induced toxicity;

(2) The polypeptide of the present invention has a wide application prospect in the prevention and treatment of amyloid diseases such as AD, PD, HD and T2DM, and lays a foundation for the treatment and diagnosis of amyloid diseases such as AD, PD, HD and T2DM.

DESCRIPTION OF THE DRAWINGS

FIG. 2 is a graph showing the binding of ZR polypeptide to a variety of amyloids detected by Dot-blot in the present invention, wherein

FIG. 3 shows the binding of ZR polypeptide derivatives to Aβ42 oligomer detected by ELISA in the present invention, wherein

FIG. 5(C) shows that the polypeptide ZR inhibited the cytotoxicity of lysozyme in vitro, and FIG. 5(D) shows that the polypeptide ZR inhibited the cytotoxicity of insulin in vitro.

FIG. 6 shows that the polypeptide of the present invention improved the spatial memory of AD transgenic mice, in which FIG. 6 (A) shows the latency for AD transgenic mice to reach the platform during the acquisition period, FIG. 6 (B) shows the latency for AD transgenic mice to reach the platform in probe trials, FIG. 6 (C) shows the number of times that the AD transgenic mice crossed the platform, FIG. 6 (D) shows the time spent by AD transgenic mice staying in the target quadrant.

FIG. 7 shows that the polypeptide of the present invention reduced the number of senile plaques in the brain of AD transgenic mice, in which FIG. 7(B) shows the area of senile plaques in the brain section, FIG. 7(C) shows the number of senile plaques in the brain section.

FIG. 8 shows that the polypeptide of the present invention reduced the levels of Aβ40 and Aβ42 in the brain of AD transgenic mice, in which FIG. 8(C) shows the level of soluble Aβ40 in the brain of AD transgenic mice, and FIG. 8(D) shows the level of soluble Aβ42 in the brain of AD transgenic mice;

FIG. 11 shows that the polypeptide of the present invention improved the motor coordination of PD transgenic mice, in which

FIG. 13 shows that the polypeptide of the present invention improved the motor coordination of HD transgenic mice, in which

DETAILED DESCRIPTION

Figure 1:
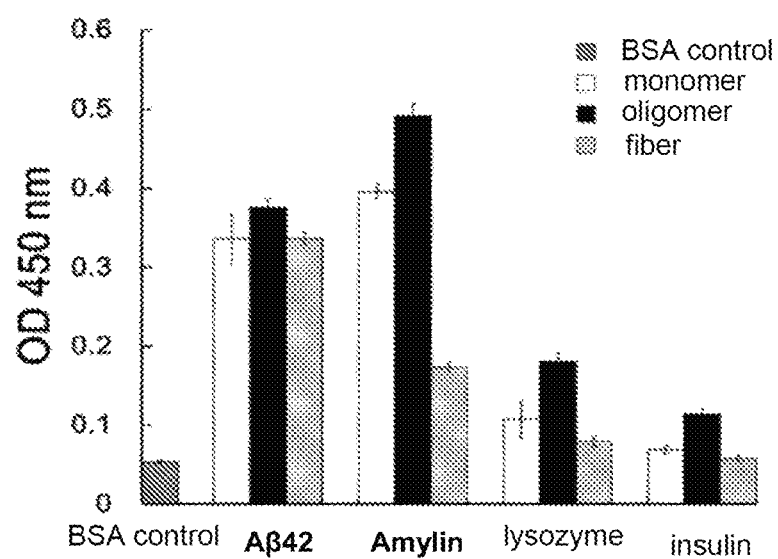
FIG. 1 is a graph showing the binding of ZR polypeptide to a variety of amyloids detected by ELISA in the present invention.

The technical solutions of the present invention will be further described with reference to specific embodiments below. It will be apparent to those skilled in the art that the illustrated examples are just for the purpose of facilitating the understanding of the present invention and should not be construed as particularly limiting the present invention.

The experimental methods used in the following examples are all conventional methods unless otherwise specified.

Materials, reagents, and etc. used in the following examples are all available from commercial sources unless otherwise specified.

The PBS buffer solution in the following examples consists of: 5.84 g NaCl, 4.72 g $Na_2HPO_4$, 2.64 g $NaH_2PO_4 \cdot 2H_2O$, adding water to a total volume of 1 L, adjusting the pH to 7.2.

Example 1 Preparation of ZR Polypeptide and Derivatives Thereof

According to the pathogenesis of amyloidosis, a basic method for treating such diseases should reduce the production of amyloids, inhibit the aggregation and cytotoxicity thereof, or accelerate the clearance of amyloids. Phage screening was performed using a phage peptide library of $1 \times 10^8$ heptapeptides through four rounds of biopanning to identify the sequences that targeted the amylin oligomers. Multiple polypeptides which significantly bind to amylin oligomers were screened out by phage ELISA. By comparing the binding properties of these polypeptides to amylin, Aβ42, PrP, insulin and lysozyme, and their effects on amyloid aggregation and cytotoxicity, the polypeptide ZR was finally chosen.

The ZR polypeptide (SEQ ID NO. 2) had a sequence of: Ser-Phe-Phe-Asn-Asn-Lys-Arg.

ZR derivatives were polypeptides obtained by substitution, deletion, or insertion of an amino acid of ZR, or insertion with another amino acid. Sequences 7-13 were obtained by alanine scanning in which the amino acids in sequence 2 were sequentially substituted by alanine; sequences 3-6 were polypeptides obtained by substitution, deletion of an amino acid of ZR, or insertion with another amino acid, as follows:

```
SEQ ID NO: 2:  Ser-Phe-Phe-Asn-Asn-Lys-Arg;

SEQ ID NO: 7:  Ala-Phe-Phe-Asn-Asn-Lys-Arg;  (control group1)

SEQ ID NO: 8:  Ser-Ala-Phe-Asn-Asn-Lys-Arg;

SEQ ID NO: 9:  Ser-Phe-Ala-Asn-Asn-Lys-Arg;  (control group2)

SEQ ID NO: 10: Ser-Phe-Phe-Ala-Asn-Lys-Arg;

SEQ ID NO: 11: Ser-Phe-Phe-Asn-Ala-Lys-Arg;  (control group3)

SEQ ID NO: 12: Ser-Phe-Phe-Asn-Asn-Ala-Arg;  (control group4)

SEQ ID NO: 13: Ser-Phe-Phe-Asn-Asn-Lys-Ala;  (control group5)

SEQ ID NO: 3 (ZR4-ΔN):  Ser-Phe-Phe-Asn-Lys-Arg;

SEQ ID NO: 4 (ZR4-FN/AQ): Ser-Ala-Phe-Gln-Asn-Lys-Arg;

SEQ ID NO: 5 (ZR + N):  Ser-Phe-Phe-Asn-Asn-Asn-Lys-Arg;

SEQ ID NO: 6 (ZR + K):  Ser-Phe-Phe-Asn-Asn-Lys-Arg-Lys.
```

The polypeptide and derivatives thereof in the following examples were synthetically prepared by GL Biochem (Shanghai) Ltd. The polypeptide with SEQ ID NO. 2 (ZR polypeptide) and derivatives thereof used for the experiments had a purity greater than or equal to 95%. The ZR polypeptide and derivatives thereof were stored at −20° C., and should be avoided from repeatedly freezing and thawing.

All the experimental data in the following examples were obtained in 3 independent experiments except for the Morris water maze test. The experimental data was expressed as average value±standard deviation. The statistical analyses were performed using one-way ANOVA, while the comparative analyses of the multiple sets of repeated measurement were performed by two-way ANOVA.

In the following examples, mice were divided into polypeptide ZR-injected group (AD+ZR), PBS-injected group (AD con), and wild-type (WT) group.

Example 2 ZR Specifically Bound to a Plurality of Amyloids

100 μL of monomers, oligomers or fibers of Aβ42, PrP, amylin, insulin or lysozyme were respectively coated onto a 96-well ELISA microplate at 1 μg/well, BSA was used as a negative control. The plate were then placed at 37° C. for 2 h, blocked with 200 μL/well of 3% BSA at 37° C. for 2 h, and washed 3 times with PBS. 100 μL of histidine-tagged ZR polypeptide solution was added, and the plate was incubated at room temperature for 1 h, and then washed 3 times with PBS containing 0.1% Tween-20. 100 μL of HRP-linked antibody 9E10 which can recognize the histidine tag was added to each well, and the plate was incubated at room temperature for 1 h, and then washed 3 times with PBS containing 0.1% Tween-20. 100 μL of TMB was added to each well, and the plate was placed at 37° C. for 20 min. Then, 50 μL of 1 mmol/L sulfuric acid was added to each well to terminate the reaction, and OD450 values were measured using a microplate reader. The above procedure was repeated for 3 times under the same condition. The results were shown in FIG. 1.

The OD450 for the binding of ZR to negative control BSA was 0.06; the OD450s for the binding of ZR to Aβ42 monomers, oligomers and fibers were 0.34, 0.38 and 0.35, respectively; the OD450s for the binding of ZR to amylin monomers, oligomers and fibers were 0.41, 0.50 and 0.18, respectively; the OD450s for the binding of ZR to lysozyme monomers, oligomers and fibers were 0.11, 0.18 and 0.08, respectively; and the OD450s for the binding of ZR to insulin monomers, oligomers and fibers were 0.07, 0.14 and 0.06, respectively;

FIG. 1 shows that the ZR polypeptide can bind to the oligomers of a plurality of amyloids such as Aβ42, amylin, PrP and lysozyme, as well as to monomers and fibers of Aβ42 and amylin, but cannot bind to monomers and fibers of PrP and lysozyme significantly. Since there is no homology between the primary amino acid sequences of these amyloids, various forms of amyloids which can simultaneously bind to the ZR polypeptide should have similar structural characteristics.

In order to further verify the binding of ZR polypeptide to various amyloids, Aβ42, PrP, amylin, insulin and lysozyme was incubated for a certain period of time, and then applied to a nitrocellulose membrane at 1.8 μg/point. After drying at room temperature, the membrane was blocked with 8% milk at 37° C. for 2 h; a histidine-tagged ZR polypeptide solution was added and incubated at room temperature for 1 h, and then the membrane was washed 3 times with PBS containing 0.1% Tween-20. Then mouse anti-histidine tag antibody was added at 1:3000 and incubated at 37° C. for 2 h; the membrane was washed 3 times with 0.1% PBST, 5 min for each time, and HRP-linked goat anti-mouse secondary antibody was added at 1:5000 and incubated at 37° C. for 1 h; the membrane was washed 3 times with 0.1% PBST, 10 min for each time. An ECL luminescent kit was used to detect the luminescent spots on the membrane with an exposure time of 3 min and a developing time of 30 s. The amyloid specific antibodies and the oligomer-specific scFv antibody W20 served as the control, the morphology of each amyloid at each time point was detected by transmission electron microscopy. The results were shown in FIGS. 2 (A)-(H).

Figure 2A:
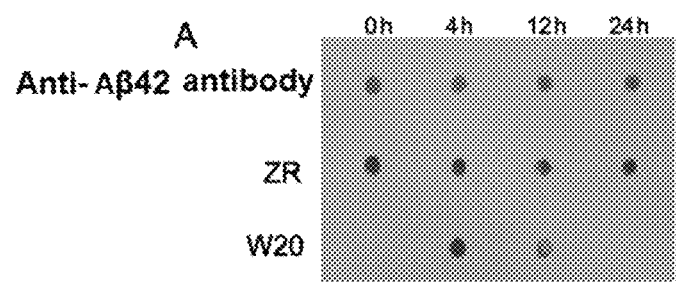
FIG. 2(A) is a graph showing the binding of ZR polypeptide to Aβ42 at each time point.
Figure 2B:
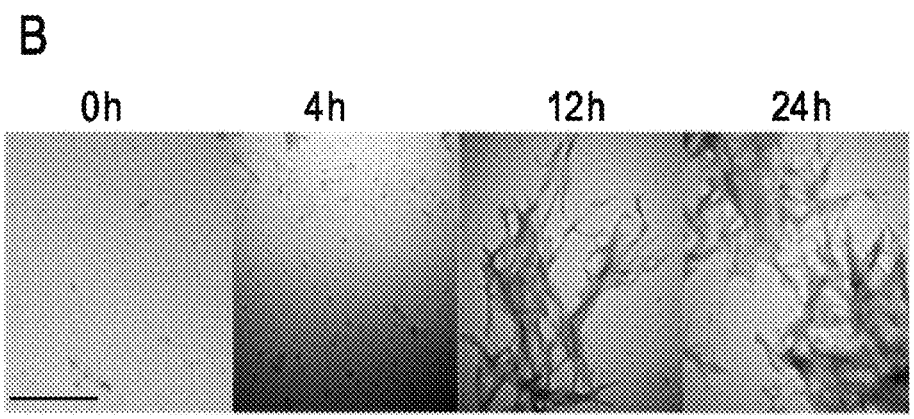
FIG. 2(B) is a morphological image showing the binding of ZR polypeptide to Aβ42 at each time point.
Figure 2C:
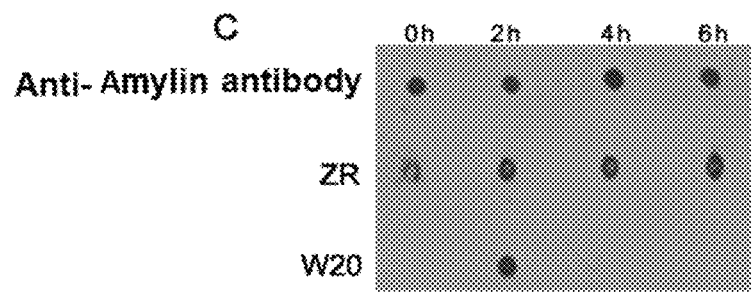
FIG. 2(C) is a graph showing the binding of ZR polypeptide to amylin at each time point.
Figure 2D:
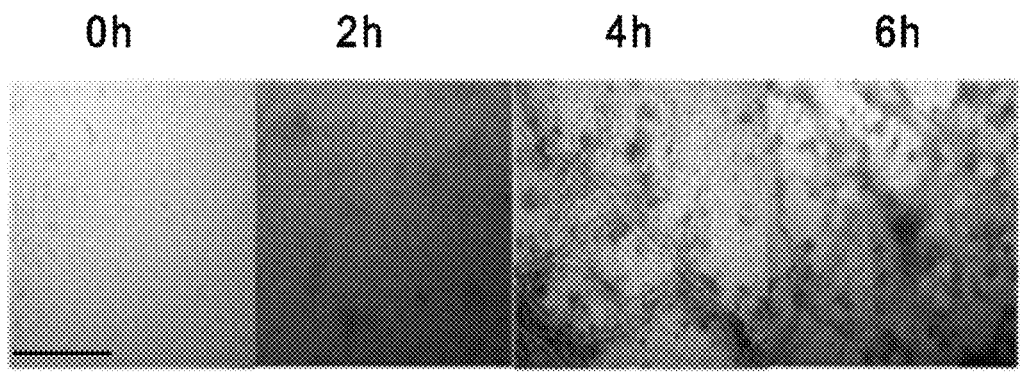
FIG. 2(D) is a morphological image showing the binding of ZR polypeptide to amylin at each time point.
Figure 2E:
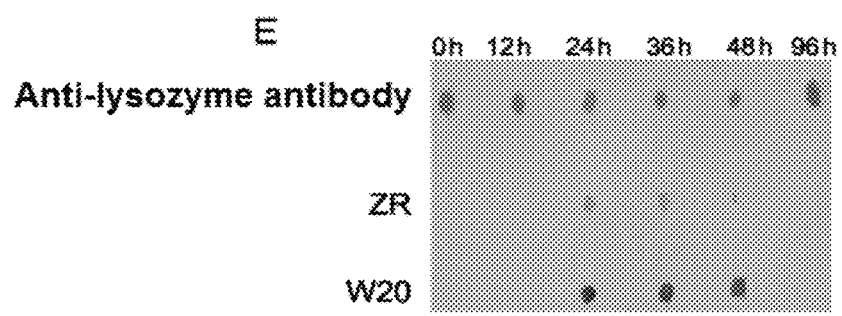
FIG. 2(E) is a graph showing the binding of ZR polypeptide to lysozyme at each time point.
Figure 2F:
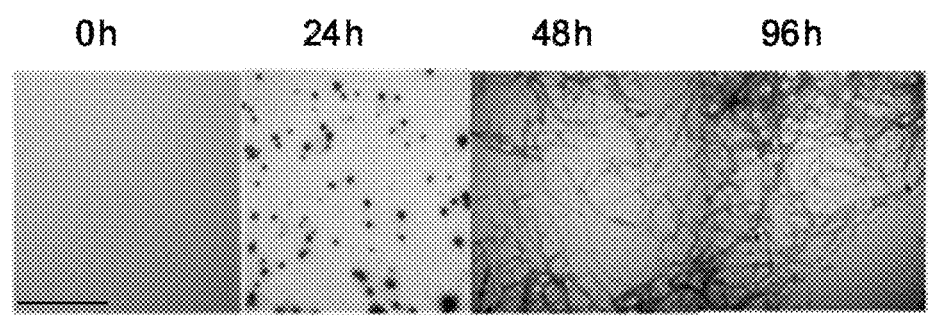
FIG. 2(F) is a morphological image showing the binding of ZR polypeptide to lysozyme at each time point.
Figure 2G:
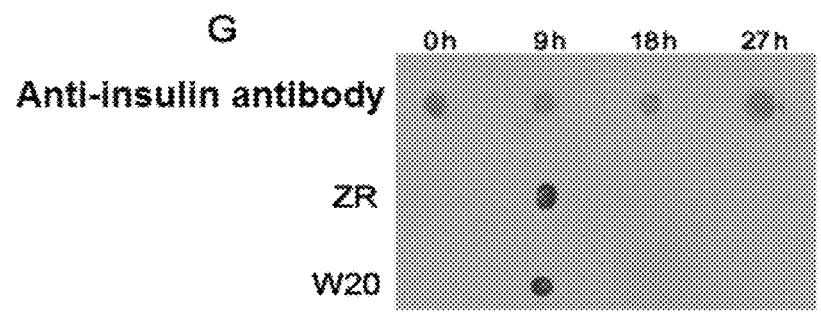
FIG. 2(G) is a graph showing the binding of ZR polypeptide to insulin at each time point.
Figure 2H:
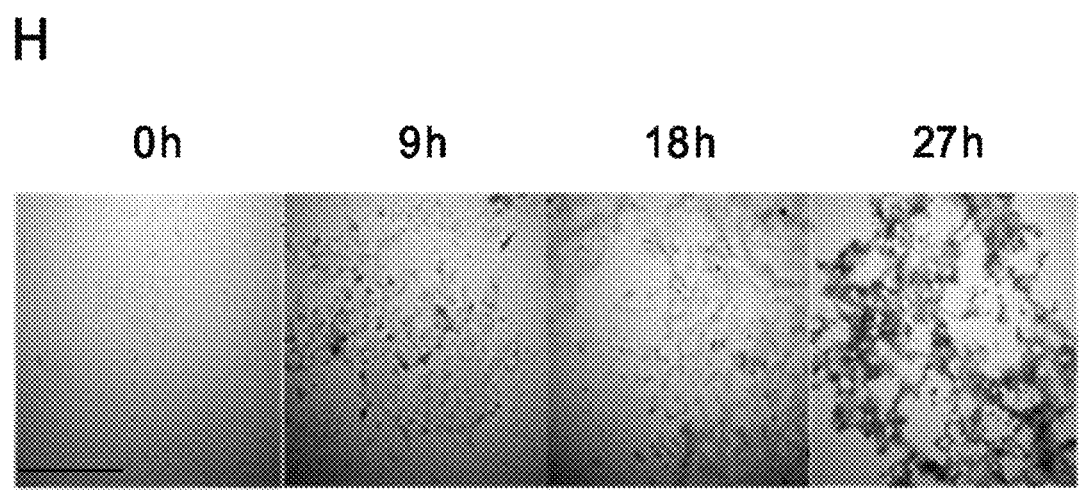
FIG. 2(H) is a morphological image showing the binding of ZR polypeptide to insulin at each time point.

FIGS. 2(A) and 2(B) showed that ZR polypeptide can bind to Aβ42 at all time points, i.e., Aβ42 monomers, oligomers and fibers. Similarly, it can be seen from FIGS. 2(C) and 2(D) that ZR polypeptide can bind to amylin at all time points, i.e., bind to amylin monomers, oligomers and fibers. However, FIG. 2(E) and FIG. 2(F) showed that ZR bound only to the lysozyme oligomers formed by incubation for 24 and 36 hours, but not its monomers and fibers. Similarly, FIG. 2(G) and FIG. 2(H) showed that ZR bound only to the insulin oligomers formed by incubation for 9 hours, but not its monomers and fibers.

Example 3 ZR Derivatives Bound to Aβ42 Oligomers

Figure 3A:
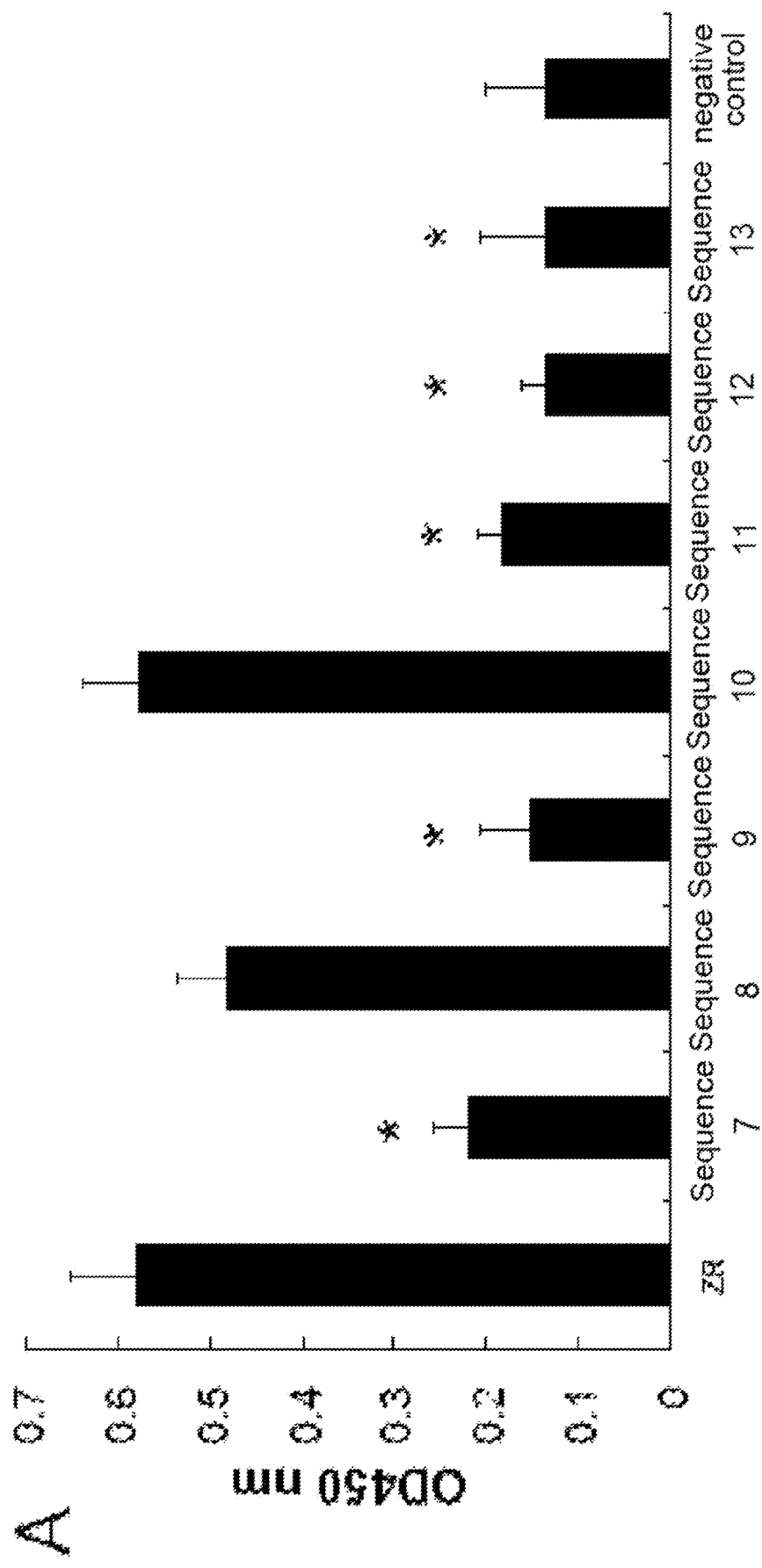
FIG. 3(A) shows the detection result of the binding of sequences 2 and 7-13 to Aβ42 oligomer.

The sequences 2-13 obtained in Example 1 were linked with a histidine tag, and their binding characteristics to Aβ42 oligomers were then detected by ELISA described in Example 2. Each polypeptide was added at 1 μg per well, and the OD450 values were measured by ELISA, the results were shown in FIGS. 3(A)-(B).

The phenylalanine at position 2 and the aspartic acid at position 4 of the ZR polypeptide sequence were substituted with alanine to create polypeptide sequences 8 and 10, respectively. It can be seen from FIG. 3(A) that the binding of these two polypeptides to Aβ42 oligomers were similar to the binding of ZR to Aβ42 oligomers. Substitution with alanine had no significant effect on the binding properties. The OD450s were 0.48 and 0.57, respectively, indicating that the phenylalanine at position 2 and the aspartic acid at position 4 had a minor effect on the binding activity of ZR polypeptide. When an amino acid at another position in ZR was substituted by alanine, its binding activity to Aβ42 oligomers was significantly lost. The OD450s were 0.22, 0.15, 0.18, 0.14, 0.14 and 0.13, respectively, when the amino acid at position 1, 3, 5, 6, or 7 was substituted with alanine respectively, indicating that the serine at position 1, the phenylalanine at position 3, the asparagine at position 5, the lysine at position 6 and the arginine at position 7 in the ZR have an important effect on the binding activity of ZR, and that the Ser-X-Phe-X-Asn-Lys-Arg structure is a basic framework structure for ZR to maintain its activity.

Figure 3B:
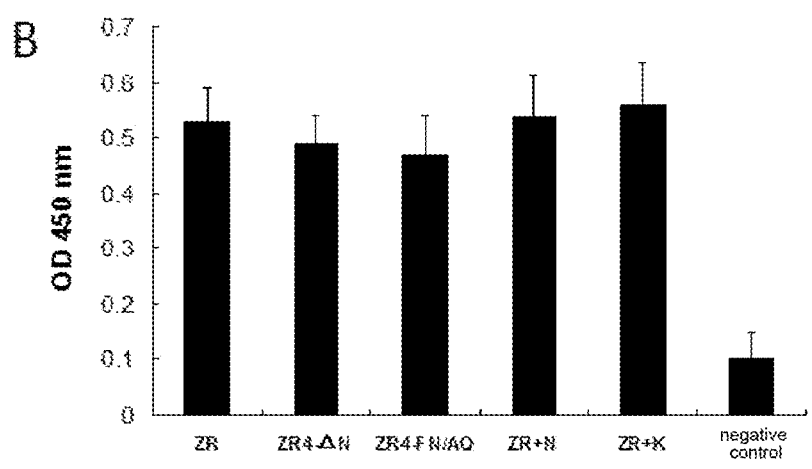
FIG. 3(B) shows the detection result of the binding of sequences 2-6 to Aβ42 oligomer.
Figure 4A:
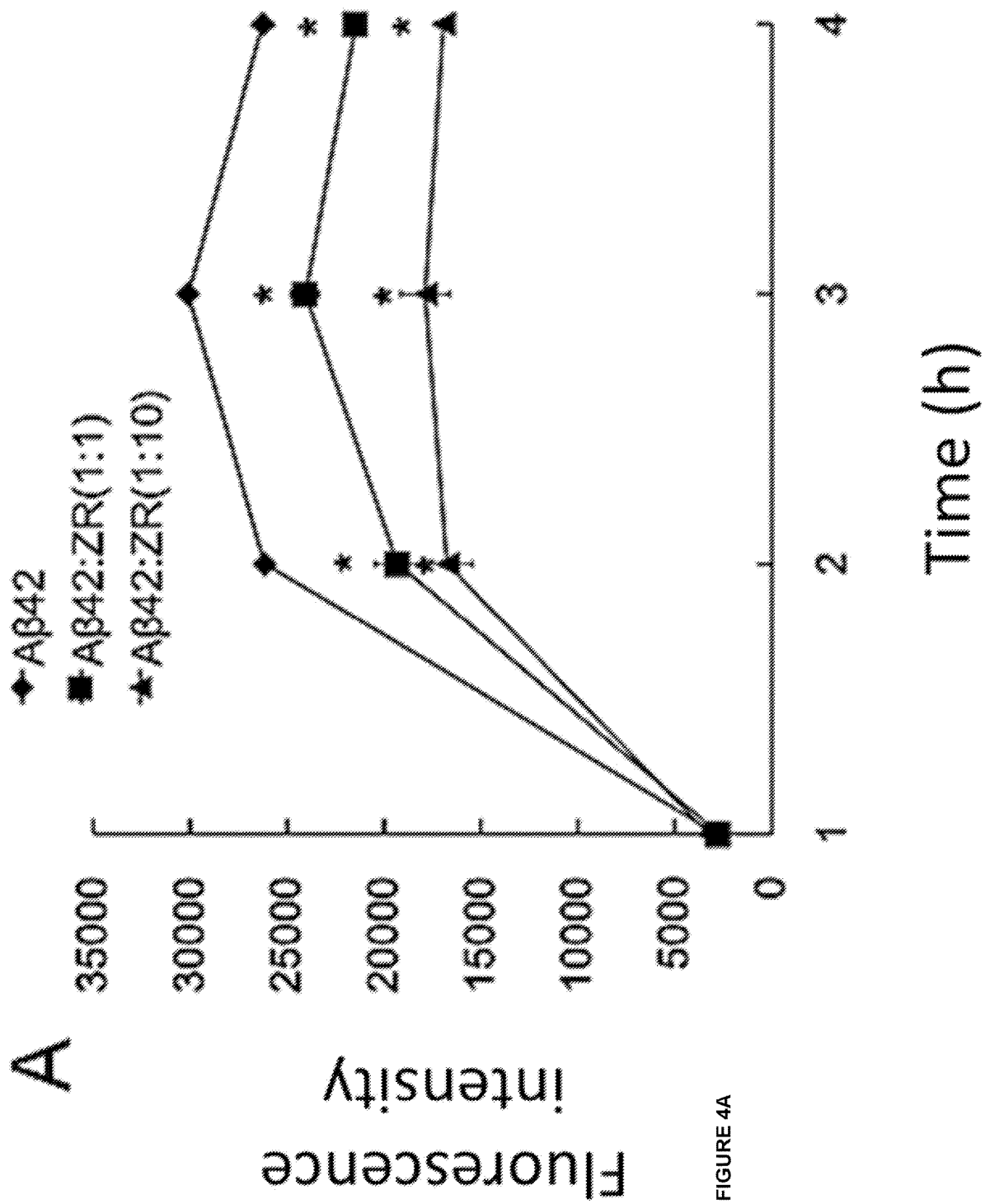
FIG. 4(A) is a graph of fluorescence intensity showing that the ZR polypeptide of the present invention inhibited the aggregation of Aβ42.
Figure 4B:
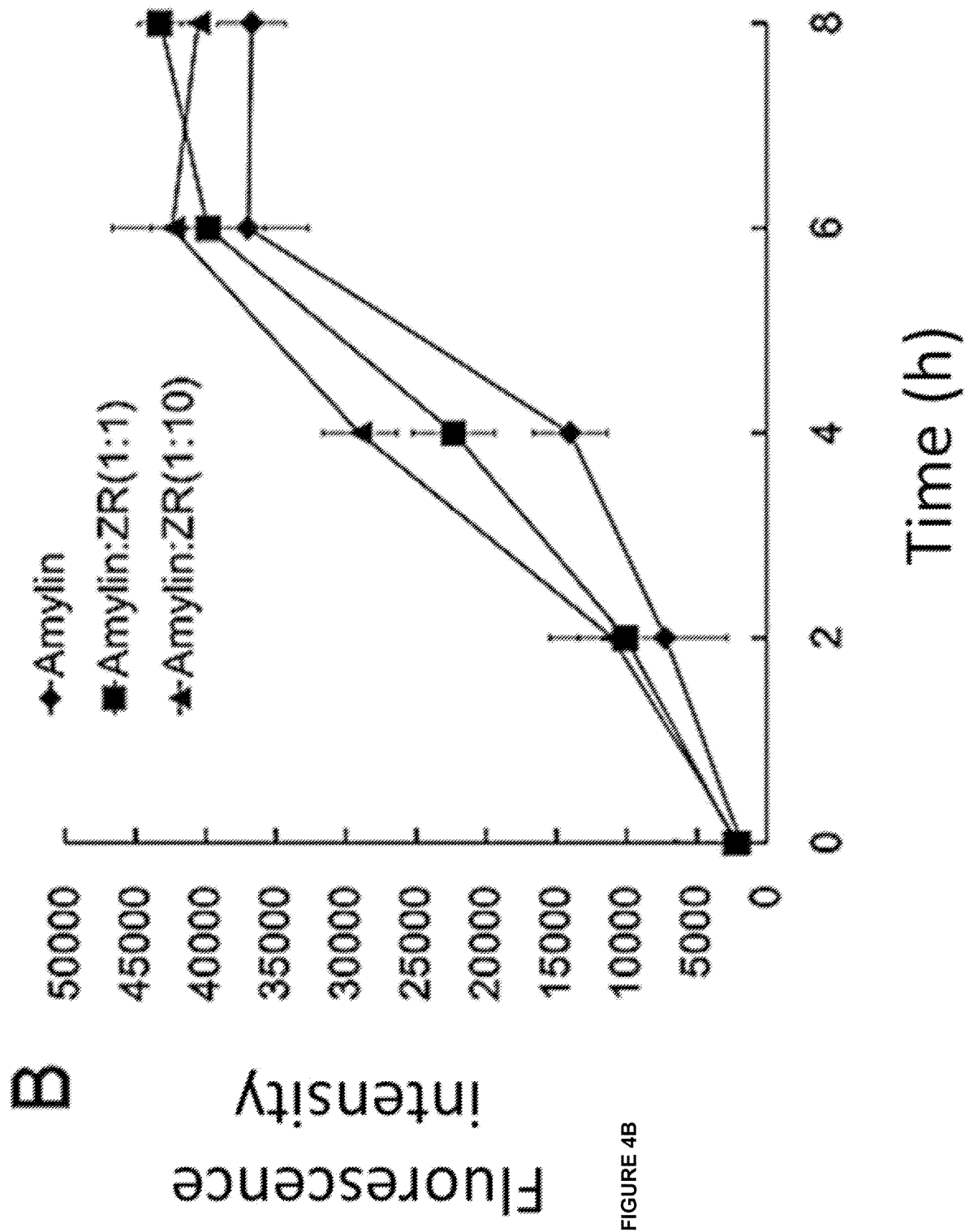
FIG. 4(B) is a graph of fluorescence intensity showing that the ZR polypeptide of the present invention inhibited the aggregation of amylin.
Figure 4C:
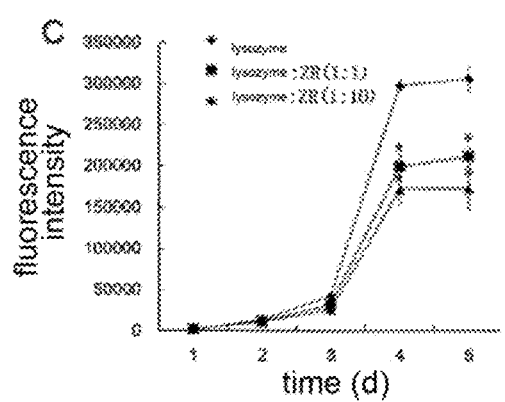
FIG. 4(C) is a graph of fluorescence intensity showing that the ZR polypeptide of the present invention inhibited the aggregation of lysozyme.
Figure 4D:
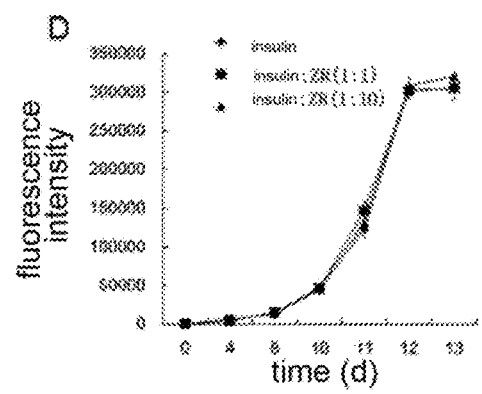
FIG. 4(D) is a graph of fluorescence intensity showing that the ZR polypeptide of the present invention inhibited the aggregation of insulin.
Figure 4E:
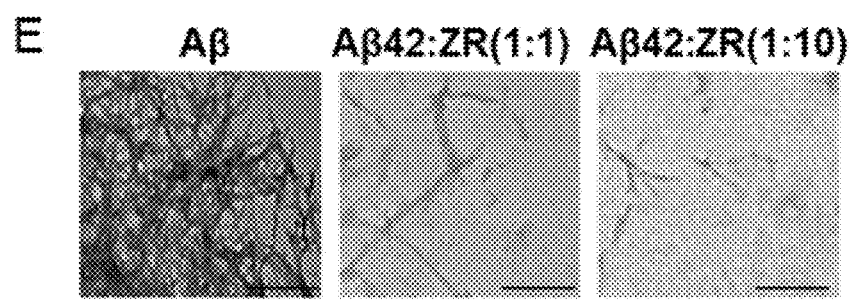
FIG. 4(E) is a transmission electron microscope morphological image showing that the ZR polypeptide of the present invention inhibited the aggregation of Aβ42.
Figure 4F:
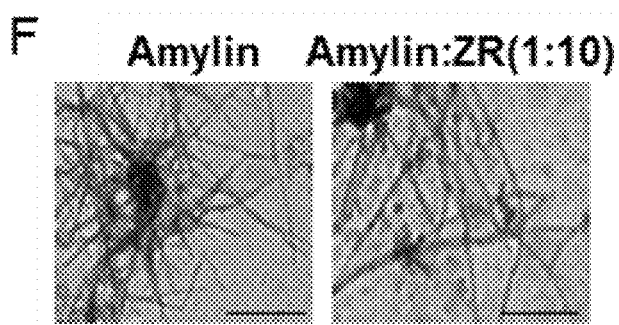
FIG. 4(F) is a transmission electron microscope morphological image showing that the ZR polypeptide of the present invention inhibited the aggregation of amylin.
Figure 4G:
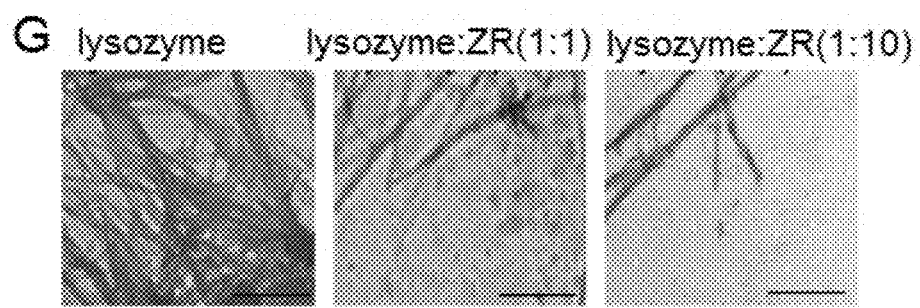
FIG. 4(G) is a transmission electron microscope morphological image showing that the ZR polypeptide of the present invention inhibited the aggregation of lysozyme.
Figure 4H:
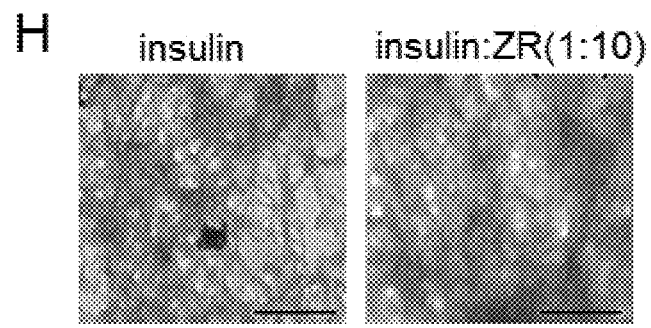
FIG. 4(H) is a transmission electron microscope morphological image showing that the ZR polypeptide of the present invention inhibited the aggregation of insulin.
Figure 5A:
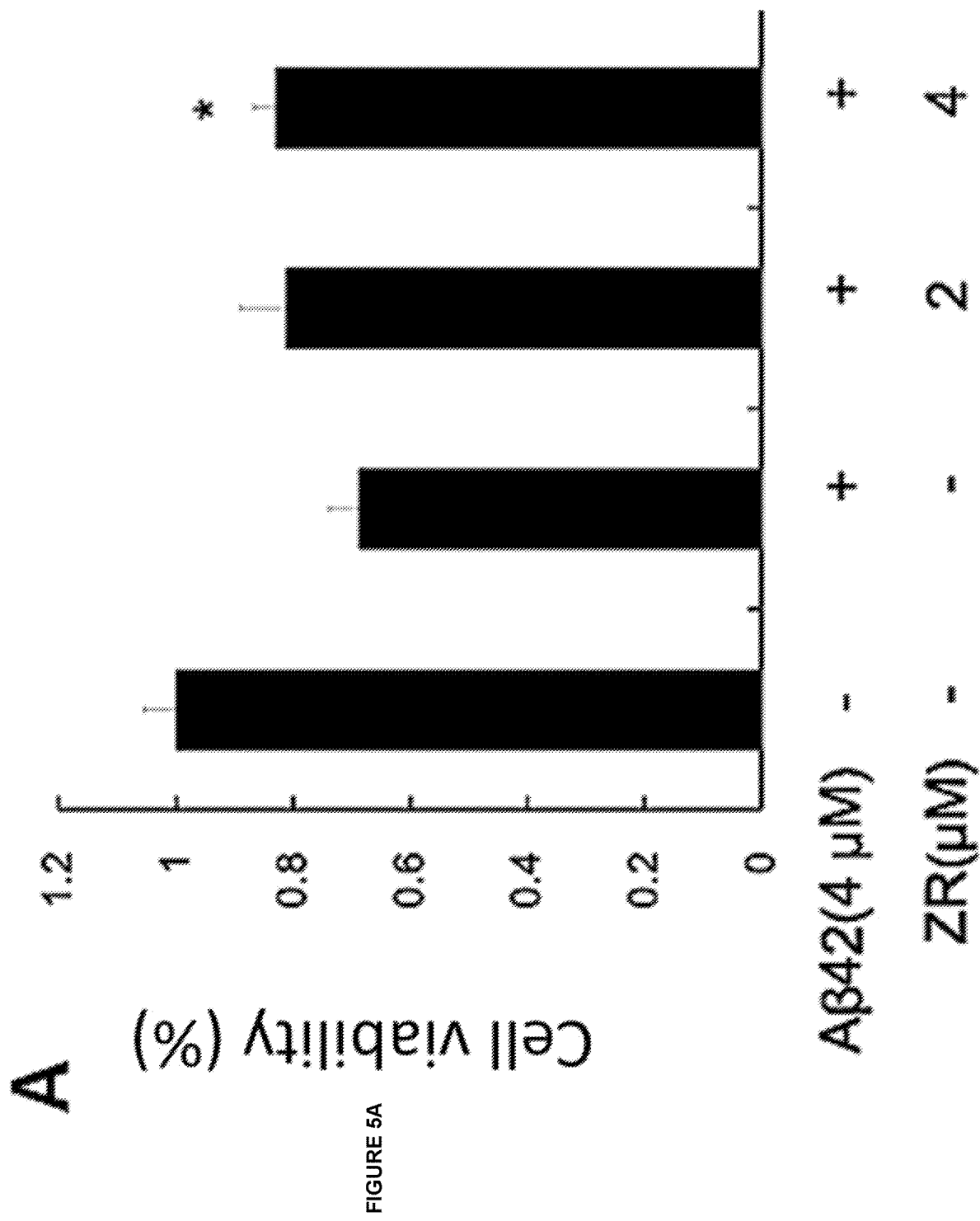
FIG. 5(A) shows that the polypeptide ZR inhibited the cytotoxicity of Aβ42 in vitro.
Figure 5B:
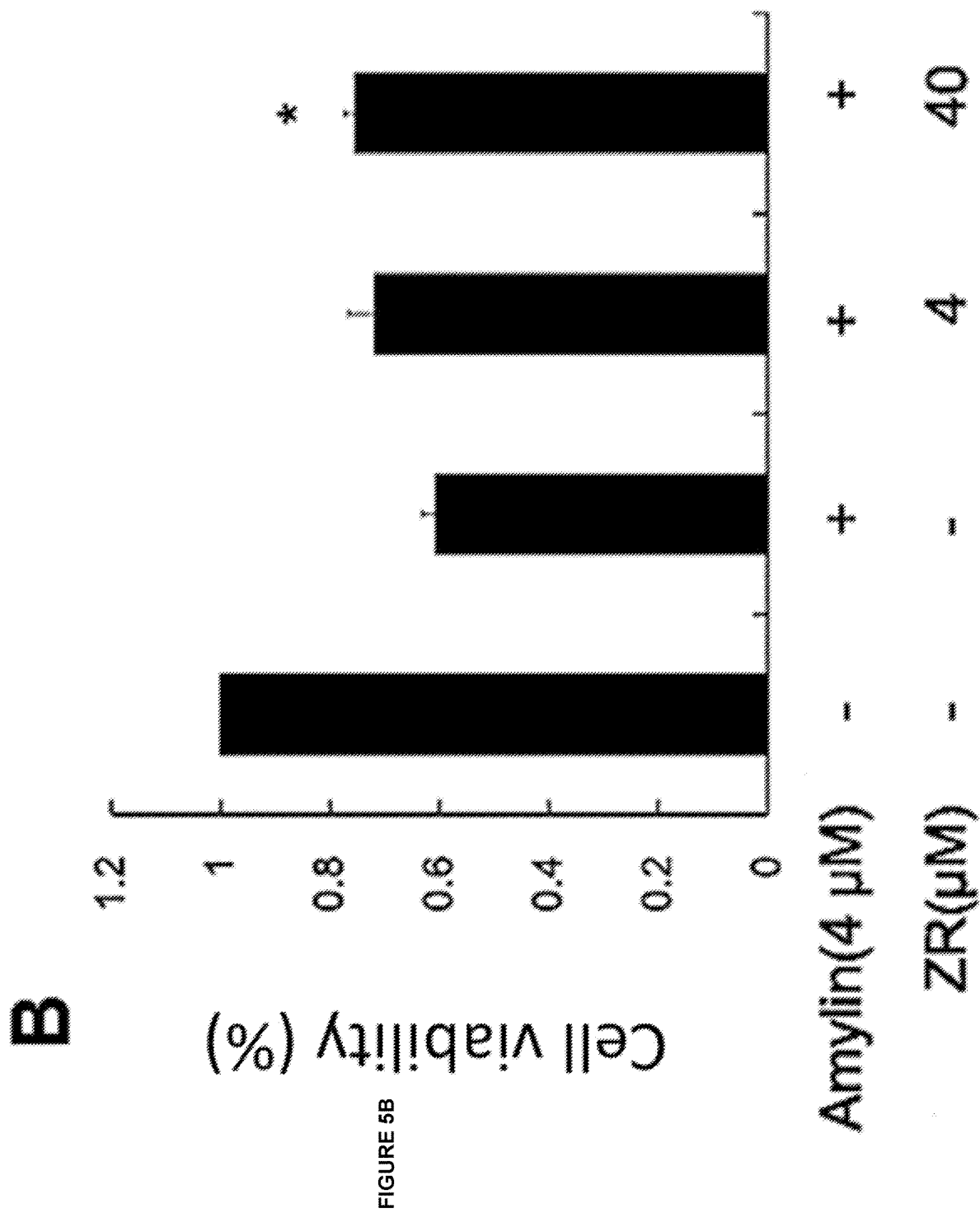
FIG. 5(B) shows that the polypeptide ZR inhibited the cytotoxicity of amylin in vitro.

FIG. 3(B) shows the ELISA results of the binding of ZR derivatives ZR4-ΔN, ZR4-FN/AQ, ZR+N and ZR+K to Aβ42 oligomers. The OD450s of these ZR derivatives binding to Aβ42 oligomers were 0.49, 0.47, 0.54 and 0.56, respectively. The results showed that ZR maintain the binding ability to Aβ42 when an amino acid therein was substituted or deleted, or an new amino acid was added into the polypeptide.

Example 4 ZR Polypeptide Inhibited the Aggregation of Aβ42 and Lysozyme In Vitro 1) Aβ42 and amylin were dissolved with hexafluoroisopropanol (HFIP) to 1 mg/mL, sonicated at room temperature for 10 min, and dispensed into Eppendorf tubes. HFIP was evaporated in vacuo. Then, the samples were stored at −20° C. Before use, the HFIP-treated proteins were placed at room temperature for 20 min, then DMSO was added to make each protein at a concentration of 5 mg/mL, and then the proteins were diluted with 0.02 M PBS buffer (pH 7.4) to the desired concentrations. PrP and lysozyme were directly prepared with 0.02 M PBS (pH 7.4) to the desired concentrations.

2) The ZR polypeptide was dissolved in 0.02 M PBS buffer (pH 7.4), then added to the solutions of Aβ42, amylin, insulin and lysozyme (acetate buffer (pH 2.5) for lysozyme, PBS (pH 7.4) for the rest) to make each protein at a final concentration of 10, 20, 100 and 1000 μM, respectively. The molar ratio of each protein to ZR polypeptide was 1:1 and 1:10, respectively. Then these samples of Aβ42, amylin and insulin were placed at 37° C., and lysozyme was placed at 65° C. for 1 day, 5 days, 5 hours and 6 days, respectively.

3) Thioflavin (ThT) was dissolved in 50 mM phosphate buffer at pH 6.5 to give a concentration of 5 μM. 20 μL of the incubated sample was added to a black ELISA plate containing 180 μL of ThT solution. After mixing, the fluorescence intensity of ThT was measured on a multi-functional microplate reader with an excitation wavelength of 450 nm and an emission wavelength of 482 nm. The background fluorescence of ThT itself was subtracted from the fluorescence intensity of each sample.

As shown in FIGS. 4(A)-(D), the fluorescence values of Aβ42 alone, Aβ42 with the addition of ZR at a molar ratio of 1:1 and 1:10 respectively, were 26500, 22000 and 17000, respectively; the fluorescence values of lysozyme alone, lysozyme with the addition of ZR at a molar ratio of 1:1 and 1:10 respectively, were 310000, 220000 and 170000, respectively; the fluorescence values of amylin alone, amylin with the addition of ZR at a molar ratio of 1:1 and 1:10 respectively, were 38000, 41000 and 43000, respectively; the fluorescence values of insulin alone, insulin with the addition of ZR at a molar ratio of 1:1 and 1:10 respectively, were 305000, 305000 and 310000, respectively.

The results showed that the fluorescence intensities of Aβ42 and lysozyme with addition of ZR were significantly lower than that of the protein itself as control. Since ThT is able to excite fluorescence only when binding to β-sheet in the amyloid aggregates, the stronger fluorescence may indicate the more amyloid aggregates. Therefore, ZR can significantly inhibit the aggregation of Aβ42 and lysozyme, but has no significant effect on the aggregation of amylin and insulin. To further verify the above results, the morphological characteristics of the various amyloids at the end of the ThT test were examined by transmission electron microscopy, as shown in FIGS. 4(E)-(H). The results showed that the addition of ZR polypeptide resulted in significant reduction in the amount of fibers formed by Aβ42 and lysozyme aggregation, while the addition of ZR had no significant effect on the aggregation of amylin and insulin.

Example 5 ZR Polypeptide Inhibited the Cytotoxicity of Amyloids In Vitro

SH-SY5Y cells were prepared into a single cell suspension with a medium (DMEM) containing 10% fetal bovine serum and then inoculated into a 96-well cell culture plate at 10000 cells per well and with a volume of 100 μL per well. The cells were incubated at 37° C., 5% of $CO_2$ concentration for 24 hours in an incubator.

The following samples were added into each well:
Aβ42: the final concentration of Aβ42 was 4 μM; a mixture of Aβ42 and ZR (Aβ:ZR=1:0.5): the final concentration of Aβ42 protein was 4 μM and the final concentration of ZR was 2 μM; a mixture of Aβ42 and ZR (Aβ: ZR=1:1): the final concentration of Aβ42 protein was 4 μM and the final concentration of ZR was 4 μM;

Amylin: the final concentration of amylin was 4 μM; a mixture of Amylin and ZR (Amylin:ZR=1:1): the final concentration of Amylin protein was 4 μM and the final concentration of ZR was 4 μM; a mixture of Amylin and ZR (Amylin: ZR=1:10): the final concentration of Amylin protein was 4 μM and the final concentration of ZR was 40 μM;

Lysozyme: the final concentration of lysozyme was 20 μM; a mixture of lysozyme and ZR (lysozyme:ZR=1:1): the final concentration of lysozyme protein was 20 μM and the final concentration of ZR was 20 μM; a mixture of lysozyme and ZR (lysozyme: ZR=1:10): the final concentration of lysozyme protein was 20 μM and the final concentration of ZR was 200 μM;

Insulin: the final concentration of insulin was 60 μM; a mixture of insulin and ZR (insulin:ZR=1:1): the final concentration of insulin protein was 60 μM and the final concentration of ZR was 60 μM; a mixture of insulin and ZR (insulin: ZR=1:5): the final concentration of insulin protein was 60 μM and the final concentration of ZR was 300 μM; PBS was used as control;

Cells were further cultured for 48 hours, then 10 μL of MTT solution was added into each well and incubated at 37° C. for 3 hours. Then the incubation was stopped by adding 100 μL dissolve solution (10% SDS and 5% iso-butanol dissolved in 0.01 M HCL) to each well, and incubated at 37° C. overnight to fully dissolve the MTT crystals. The absorbance of each well was measured on a multifunctional ELISA reader at a wavelength of 570 nm. After subtracting the background, the absorbance of the sample was divided by the absorbance of PBS control to act as an indicator of the cell activity, and the significant differences were analyzed. The results were shown in FIGS. 5(A)-(D).

The cell activity in the Aβ42 group was 71%; the cell activity in the Aβ:ZR=1:0.5 group was: 80%; the cell activity in the Aβ:ZR=1:1 group was: 82%; the cell activity in the Amylin group was: 61%; the cell activity in the Amylin: ZR=1:1 group was: 70%; the cell activity in the Amylin:ZR=1:10 group was: 75%; the cell activity in the lysozyme group was: 55%; the cell activity in the lysozyme: ZR=1:1 group was: 85%; the cell activity in the lysozyme: ZR=1:10 group was: 93%; the cell activity in the insulin group was: 77%; the cell activity in the insulin: ZR=1:1 group was: 92%; the cell activity in the insulin: ZR=1:5 group was: 102%.

The results showed that amyloids were cytotoxic to SH-SY5Y cells at certain concentration. ZR significantly reduced the cytotoxicity of amyloids dose-dependently. The cytotoxicity induced by Aβ42, amylin, lysozyme and insulin was inhibited by 37.8%, 45.4%, 117.6% and 89.8%, respectively, when the molar ratios of ZR to Aβ42, amylin, lysozyme and insulin were 1:1, 1:10, 1:10 and 1:5, respectively. Therefore, ZR can significantly inhibit the cytotoxicity of Aβ42, amylin, lysozyme and insulin, regardless of the distinct effect of ZR polypeptide on the aggregation of each amyloid.

Example 6 ZR Polypeptide Improved the Spatial Memory of AD Transgenic Mice

1) Intracerebroventricular injection: 8-month-old female APP/PS1 AD transgenic mice were randomly divided into ZR-injected group (AD+ZR) and PBS-injected group (AD con), with 8 mice per group. Their WT littermates of the same age were used as control (WT). All the mice were treated as follows:

Mice were fasted for 12 hours before intracerebral injection and allowed to drink water ad-libitum. The mice were anesthetized at such an anesthetic dose that: 0.1 mL chloral hydrate at a concentration of 10% was intraperitoneally injected into a 25 g mouse. The mice were placed on a stereotaxic apparatus and dosed through stereotaxic intracerebroventricular injection referring to the standard map. The injection coordinates were 1.8 mm caudal to bregma, 1.8 mm lateral to midline, and 2.5 mm ventral to the brain surface of the skull. ZR was dissolved in sterile water at 1 mg/ml. The injection rate was 0.2 μl/min, and the injection volume was 5 μl. After injection, the needle was retained for 5 min to ensure adequate diffusion of agents and then was slowly retracted. The injection was performed every 7 days for a total of 4 injections. Five days after the last injection, the mice were subjected to Morris water maze test.

2) Memory training: Mice were allowed to acclimate for 3 days at room temperature of 25° C. and humidity of 46% before the Morris water maze training. A randomized, double-blind manner was used for all behavioral tests. Before training, the platform was removed and a mouse was gently placed in the center of the pool and was allowed to swim freely for 60 s. The swimming quadrant preference was determined for mice and the opposite wall of the preferred quadrant was selected as the initial release position of the mice. Before the first training, the mouse was allowed to stand on the platform (with a diameter of 10 cm) for 15 s to remember the spatial position of the platform within the pool (with a diameter of 1.1 m). The upper surface of the platform was 1.5 cm away from the surface of water. Milk powder was added to water in the pool to increase the visual contrast of animal and facilitate image recording. The mouse was placed into water gently facing towards the wall of the pool and was allowed to swim freely in the pool. The mouse stood on the platform for 2 s was regarded as reaching the platform. The training time was up to 60 s for each test. During this process, the trajectory and the time to reach the platform, i.e., latency, were recorded. The mouse was allowed to stay on the platform for 10 s after finding the platform within 60 s. If the mouse did not find the platform within 60 s, it was guided to the platform and stay on it for 10 s. The mice were trained twice per day over five consecutive days, with an inter-trial interval of 3-4 h. Then, 24 h later, the platform was removed and the mouse was allowed to search for the platform for 60 s. The results of the five-day training and the probe trial were recorded via a video tracking system.

The experiment results were shown in FIGS. 6 (A)-(D). The latency for each group of mice to find platform was gradually shortened during the training period; the details were as follows:

On the 3rd, 4th and 5th days of the training, the latency of the AD mice treated with ZR to find the platform was significantly shorter than those for AD control mice. FIG. 6(A) showed that the AD mice treated with ZR had significant improved spatial memory than AD control mice; FIG. 6 (B) shows that after removing the platform, the latency for the AD mice treated with ZR to find platform were also significantly lower than those for AD control mice. The latency for the WT mice, the AD control mice and the ZR-treated AD mice were 16 s, 24 s and 17 s, respectively; FIG. 6(C) showed that the number of platform crossing of AD mice treated with ZR was significantly higher than that of the AD mouse control. The number of platform crossing of WT mice, AD control mice and ZR-treated AD mice were 4.2, 1.8 and 3.7, respectively; FIG. 6(D) showed that AD mice treated with ZR spent more time in target quadrant than AD control mice. The time spent in target quadrant of WT mice, AD control mice and ZR-treated AD mice was 20 s, 11 s and 19 s, respectively. These results indicated that ZR treatment reversed the memory deficits in AD transgenic mice.

Example 7 ZR Polypeptide Reduced the Number of Senile Plaques in the Brain of AD Transgenic Mice 1) Mice of ZR-injected (AD+ZR) group, the PBS-injected group (AD con) and WT group as described above were subjected to heart perfusion. Brains were harvested and frozen immediately with liquid nitrogen, and stored at −80° C. Before use, the frozen brain tissues were cut with a cryostat microtome to obtain sections with a thickness of 16 μm. One section was selected at intervals of 9 sections for staining.

2) The sections were stained with 1 mg/mL ThS for 10 min and then washed 3 times with 70% ethanol.

3) Images were collected by using a fluorescence microscope at an excitation wavelength of 488 nm and observed with a 4× objective lens. The results were shown in FIGS. 7(A)-(C).

Figure 7A:
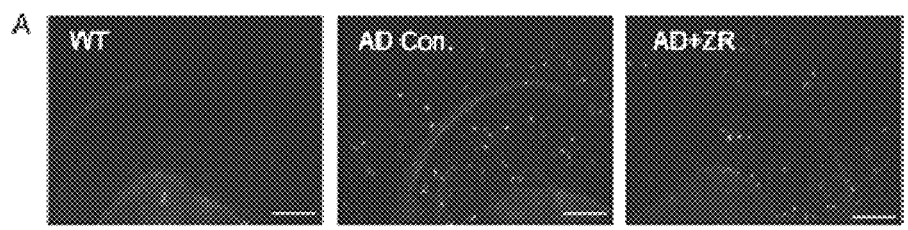
FIG. 7(A) shows the ThS staining of senile plaques in the mice.

FIG. 7(A) showed the area of senile plaques in brain sections (10-12 sections per mouse) of the WT mice, ZR-injected (AD+ZR) group (n=8) and PBS-injected group (AD con) (n=8). The number of senile plaques in the brain of the AD mice injected with ZR was significantly reduced. FIGS. 7(B) and (C) showed that the senile plaque area and the number of senile plaques were 0.3% and 4 per $mm^2$, respectively, in brain sections of ZR-injected (AD+ZR) group, while the senile plaque area and the number of senile plaques were 1.7% and 17 per $mm^2$, respectively, in brain sections of PBS-injected group (AD con). Statistical analyses showed that the number and area of senile plaques in the brain of the AD mice injected with ZR were significantly decreased.

The above frozen sections were treated in 0.3% hydrogen peroxide and then blocked with 10% goat serum. Anti-Aβ antibody 6E10 diluted at 1:3000 was added and incubated at 37° C. for 1 h, then biotinylated goat anti-mouse secondary antibody was added and incubated at 37° C. for 1 h, and finally HRP-linked streptavidin was added. Diaminobenzidine (DAB) was used as a substrate for visualization, and images were acquired with a microscope.

Figure 7D:
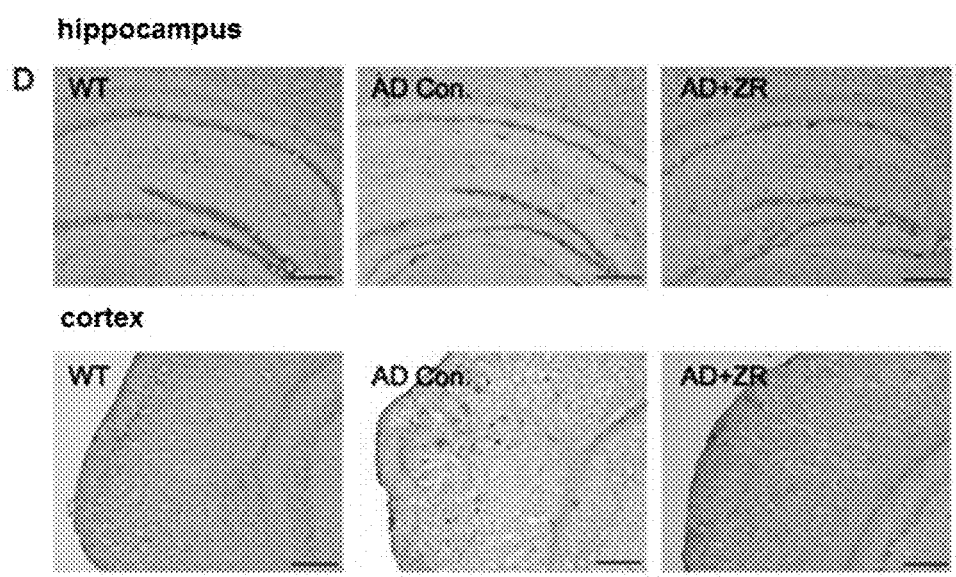
FIG. 7(D) shows the 6E10 staining of senile plaques in the mice.
Figure 7E:
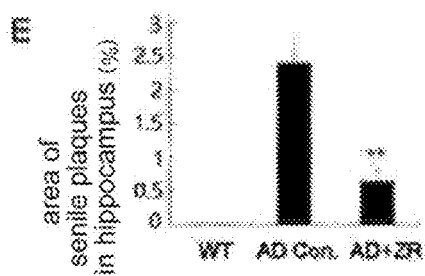
FIG. 7(E) shows the area of senile plaques in the hippocampus of the mice.
Figure 7F:
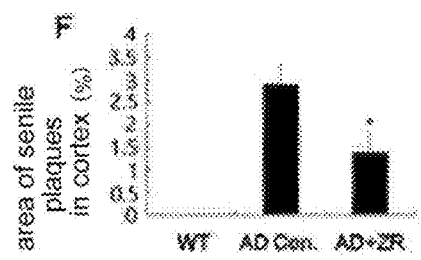
FIG. 7(F) shows the area of senile plaques in the cortex of the mice.
Figure 7G:
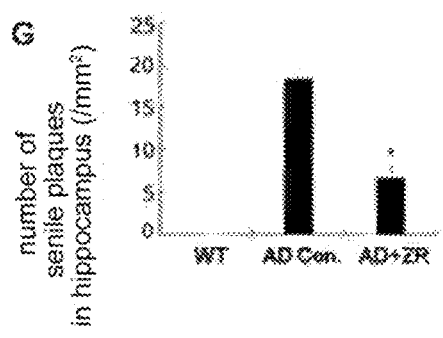
FIG. 7(G) shows the number of senile plaques in the hippocampus of the mice.
Figure 7H:
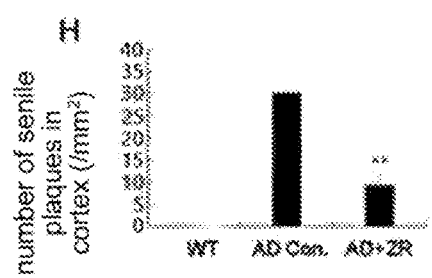
FIG. 7(H) shows the number of senile plaques in the cortex of the mice.
Figure 8A:
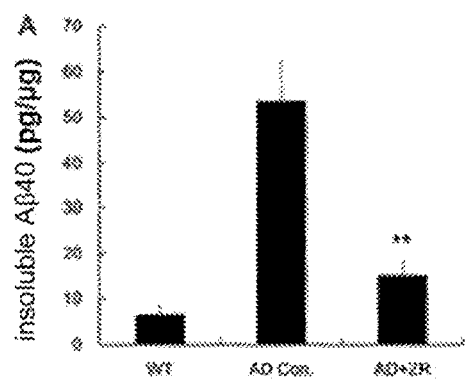
FIG. 8(A) shows the level of insoluble Aβ40 in the brain of AD transgenic mice.
Figure 8B:
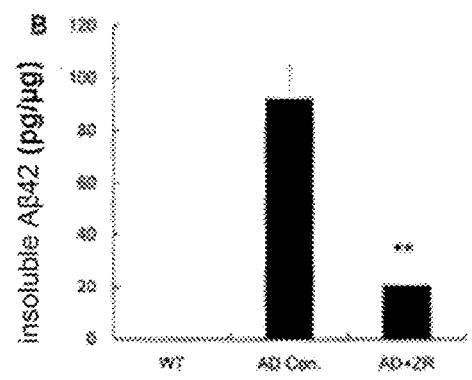
FIG. 8(B) shows the level of insoluble Aβ42 in the brain of AD transgenic mice.

FIG. 7(D) showed that the number of senile plaques in hippocampus and cortex of the AD control mice was significantly greater than that of the AD mice treated with ZR. The area and number of senile plaques in brain sections (10-12 sections per mouse) of ZR-injected (AD+ZR) group (n=8) and the PBS-injected group (AD+con or control) (n=8) were determined as FIGS. 7 (E)-(H):

The area of senile plaques in the hippocampus of mice injected with ZR was 0.7%, and the area of senile plaques in the hippocampus of mice injected with PBS was 2.4%; the area of senile plaques in the cortex of mice injected with ZR was 1.3%, and the area of senile plaques in the cortex of mice injected with PBS was 2.9%; the number of senile plaques in the hippocampus of mice injected with ZR was 7 per $mm^2$, and the number of senile plaques in the hippocampus of mice injected with PBS was 18 per $mm^2$; the number of senile plaques in the cortex of mice injected with ZR was 9 per $mm^2$, and the number of senile plaques in the cortex of mice injected with PBS was 30 per $mm^2$; statistical analyses showed that the number and area of senile plaques in hippocampus and cortex of the AD mice injected with ZR were significantly decreased.

Example 8 ZR Polypeptide Reduced Aβ40 and Aβ42 Levels in the Brain of AD Transgenic Mice The brain tissues of mice of ZR-injected (AD+ZR) group and the PBS-injected group (AD control) as described above were homogenized in pH 7.2 PBS containing protease inhibitors, then centrifuged at 15000 rpm for 30 min, and the supernatant was collected. 5M guanidine hydrochloride (prepared with tris-HCl buffer, pH 8.0) was added to the precipitate, then centrifuged, and the supernatant was collected. Aβ levels were determined by an ELISA kit. The results were shown in FIG. 8(A)-(D).

FIG. 8 (A) showed that the Aβ40 level in the brain of mice injected with ZR was 17 pg/μg, and the Aβ40 level in the brain of mice injected with PBS was 56 pg/μg; FIG. 8 (B) showed that the Aβ42 level in the brain of mice injected with ZR was 23 pg/μg, and the Aβ42 level in the brain of mice injected with PBS was 97 pg/μg; FIG. 8 (C) showed that the Aβ40 level in the brain of mice injected with ZR was 4 pg/μg, and the Aβ40 level in the brain of mice injected with PBS was 7.4 pg/μg; FIG. 8 (D) showed that the Aβ42 level in the brain of mice injected with ZR was 2.4 pg/μg, and the Aβ42 level in the brain of mice injected with PBS was 5.1 pg/μg.

Statistical analyses showed that the levels of soluble and insoluble Aβ40 and Aβ42 levels in the brain of AD mice injected with ZR were significantly lower than those of mice injected with PBS.

Example 9 ZR Polypeptide Reduced Inflammation Level in the Brain of AD Transgenic Mice The frozen brain sections were treated in 0.3% hydrogen peroxide and the sections were then blocked with 10% goat serum. Anti-Iba-1 antibody diluted at 1:200 and anti-GFAP antibody diluted at 1:100 were added respectively and incubated at 37° C. for 1 h, then biotinylated secondary antibody was added and incubated at 37° C. for 1 h, and finally HRP-linked streptavidin was added. Diaminobenzidine (DAB) was used as a substrate for visualization, and images were acquired with a microscope.

The area of microglia and astrocytes in brain sections (10-12 sections per mouse) of ZR-injected (AD+ZR) group (n=8) and PBS-injected group (AD con) (n=8) were determined.

Figure 9A:
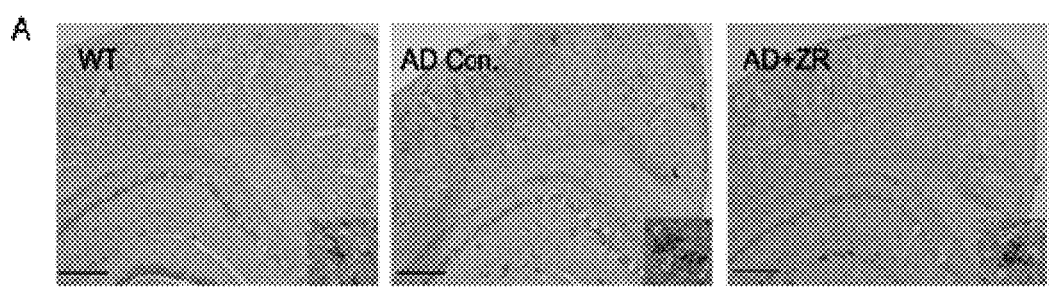
FIG. 9 shows that the polypeptide of the present invention reduced the inflammatory response in the brain of AD transgenic mice, in which FIG. 9 (A) shows the staining of microglia cells in the brain of AD transgenic mice, FIG. 9 (B) shows the staining of astrocytes in the brain of AD transgenic mice, FIG. 9 (C) shows the area of microglia cells in the brain section of AD mice.
FIG. 9(D) shows the area of astrocytes in the brain section of AD mice.
Figure 9B:
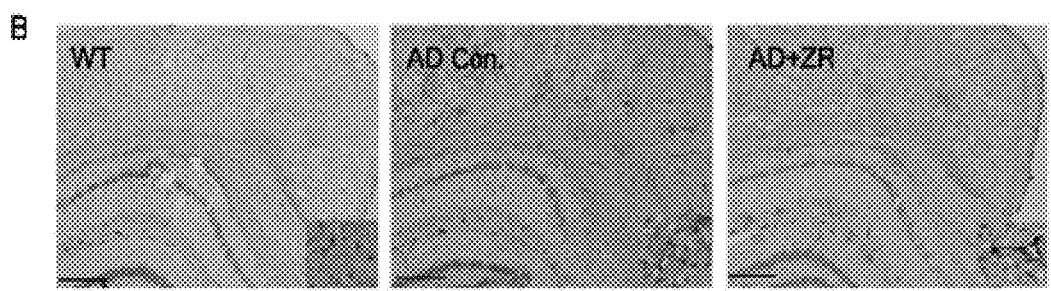
Figure 9C:
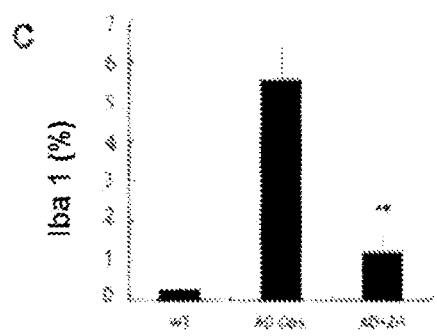
Figure 9D:
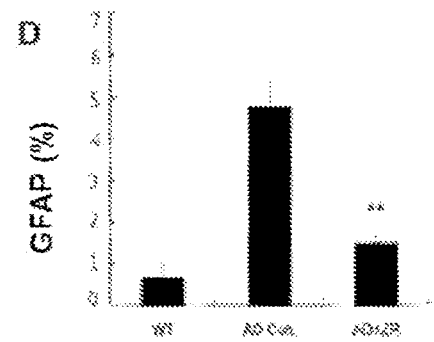

FIGS. 9(A) and (B) showed that the numbers of microglia and astrocytes in the brain of the AD mice injected with ZR were significantly reduced. FIGS. 9(C) and (D) showed that microglia in the brain of the AD mice injected with ZR accounted for 1.2% of the area of brain section, while microglia in the brain of the AD mice injected with PBS accounted for 5.7% of the area of brain section; astrocytes in the brain of the AD mice injected with ZR accounted for 1.8% of the area of the brain section, while astrocytes in the brain of the AD mice injected with PBS accounted for 4.9% of the area of the brain section.

Statistical analyses showed that the numbers of microglia and astrocytes in the brain of AD mice injected with ZR were significantly reduced.

Example 10 ZR Polypeptide Promoted Phagocytosis of Aβ by Cells

BV-2 cells were prepared into a single cell suspension with DMEM medium containing 10% fetal bovine serum and inoculated into a 96-well cell culture plate at 10000 cells per well and with a volume of 100 μL per well. The cells were incubated at 37° C., 5% of $CO_2$ for 24 hours in an incubator, and then the following substances were added respectively:

Aβ42: the final concentration of Aβ42 was 0.1 μM; the molar ratio of Aβ42:ZR=1:50: the final concentration of Aβ42 protein was 0.1 μM, and the final concentration of ZR was 5 μM; the molar ratio of Aβ42:ZR=1:100: the final concentration of Aβ42 protein was 0.1 μM, and the final concentration of ZR was 10 μM; the molar ratio of Aβ42:ZR=1:200: the final concentration of Aβ42 protein was 0.1 μM, and the final concentration of ZR was 20 μM.

Figure 10:
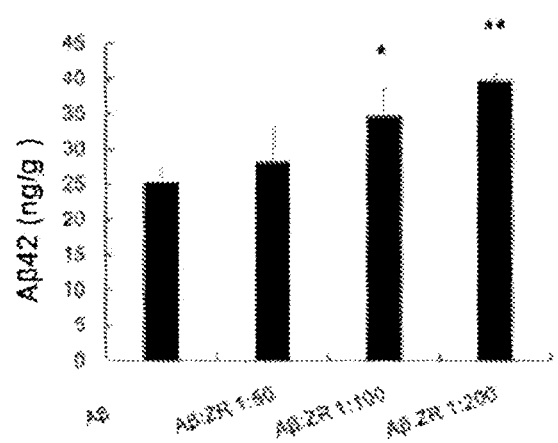
FIG. 10 shows that the polypeptide of the present invention promoted phagocytosis of Aβ by microglia.

Cells were further cultured for 4 h, and then the cell lysates were collected. Aβ42 levels in the cells were determined by an Aβ detection ELISA kit. The results were shown in FIG. 10:

the molar ratio of Aβ42:ZR=1:0: Aβ42 protein had a concentration of 26 ng/g; the molar ratio of Aβ42:ZR=1:50: Aβ42 protein had a concentration of 28 ng/g; the molar ratio of Aβ42:ZR=1:100: Aβ42 protein had a concentration of 33 ng/g; the molar ratio of Aβ42:ZR=1:200: Aβ42 protein had a concentration of 38 ng/g.

The Aβ42 level in BV-2 cells was gradually increased as the increased concentration of the added ZR, indicating that ZR had an effect of promoting microglia cells to phagocyte Aβ.

Example 11 ZR Polypeptide Improved the Motor Coordination of PD Transgenic Mice 1) Intracerebroventricular injection: 9-month-old PD transgenic mice were randomly divided into ZR-injected group (AD+ZR) and PBS-injected group (PD control), with 8 mice per group. Their WT littermates of the same age were used as control (WT). All the mice were treated as follows:

Mice were fasted for 12 hours before intracerebral injection and allowed to drink water ad-libitum. The mice were injected in the same manner as in example 6 and subjected to a pole test and a hindlimb clasping test.

Figure 11A:
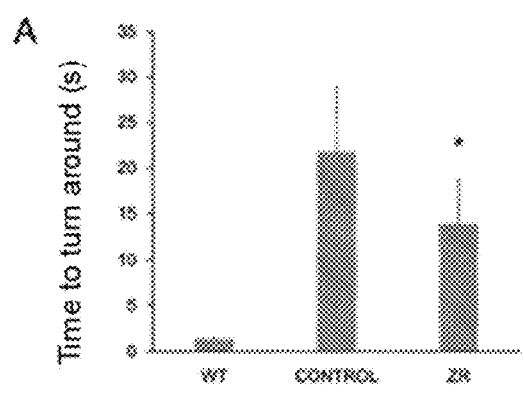
FIG. 11(A) shows the time for PD transgenic mice to turn around in pole test.
Figure 11B:
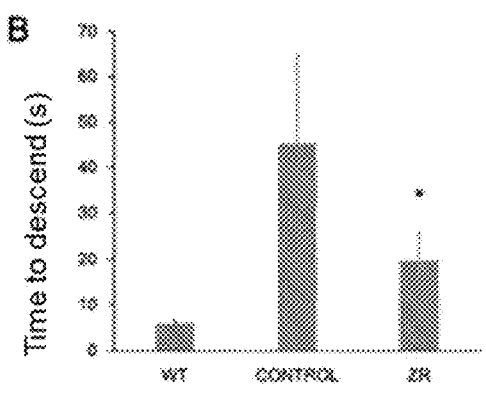
FIG. 11(B) shows the time for PD transgenic mice to descend from the pole.

2) Pole test: A rough-surfaced wooden pole (50 cm in length and 1 cm in diameter) with a base was used. During the test, mice were placed with their heads oriented toward the top of the pole. The time required by the mouse to turn its head downward and descend the entire length of the pole was measured. The time to turn around would be recorded as 30 s and the time to descend would be recorded as 60 s if the mouse fell off, slid off, or failed to complete the task. The test was conducted as five consecutive trials for 3 consecutive days, the first two days being training period, and the third day being testing period. Statistical analyses were performed for the time to turn around and time to descend during the testing period. The results were shown in FIG. 11(A)-(B):

The time for WT mice, PD control mice and ZR-treated PD mice to turn around was 1.38 s, 21.87 s and 13.9 s, respectively, and the time to descend was 6.02 s, 45.48 s and 19.74 s, respectively. Statistical analyses showed that the time for PD mice treated with ZR to turn around and to descend in the pole test were significantly lower than those of PD control mice.

Figure 11C:
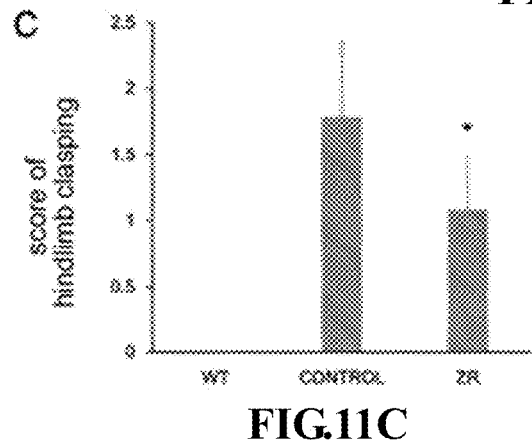
FIG. 11(C) shows the hindlimb clasping scores of PD transgenic mice.

3) Hindlimb clasping test: Mice were suspended by the base of the tail and videotaped for 15 s. Hindlimb clasping was rated from 0 to 3 based on severity: 0=hindlimbs splayed outward and away from the abdomen; 1=one hindlimb retracted inward toward the abdomen for at least 50% of the observation period; 2=both hindlimbs partially retracted inward toward the abdomen for at least 50% of the observation period; and 3=both hindlimbs completely retracted inward toward the abdomen for at least 50% of the observation period. Scores of 0.5 were utilized when appropriate. Hindlimb clasping severity scores were averaged for the three separate trials over three consecutive days. The results were shown in FIG. 11(C):

The hindlimb clasping scores for WT mice, PD control mice, and ZR-treated PD mice were 0, 1.78 and 1.08, respectively. Statistical analyses showed that ZR treatment significantly attenuated the hindlimb clasping behavior in PD mice.

Example 12 ZR Polypeptide Reduced α-Synuclein Level in the Brain of PD Transgenic Mice Mice of ZR-injected (PD+ZR) group, PBS-injected group (PD control) and WT group were subjected to heart perfusion, and the brain stem and cerebellum were harvested and weighed. The brain tissues were added, at a ratio of 1:5 (V/W), to THE buffer (10 mM Tris HCl pH 7.4; 150 mM NaCl; 5 mM EDTA) containing 1× protease inhibitor and 0.5% NP40, homogenized on ice for 5 min, left for 20 min, and then centrifuged at 4° C. at a centrifugal force of 100,000 g for 5 min, and the supernatant was collected.

Figure 12:
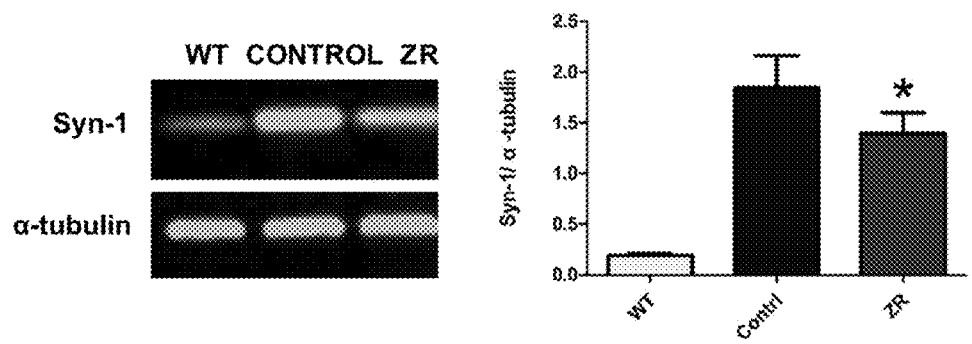
FIG. 12 shows that the polypeptide of the present invention reduced α-synuclein level in the brain of PD transgenic mice.

Protein samples were prepared by mixing LDS buffer, reducing agent and brain lysates thoroughly in a total volume of 10 μL, followed by incubation in a metal bath at 70° C. for 10 min, and then centrifuged at 12,000 rpm at room temperature for 5 min 4-12% Bis-Tris NuPAGE gel was used, with 10 μl of sample loaded per well, and electrophoresed at 150 V for 80 min. Then the proteins were transferred onto a nitrocellulose membrane at 300 mA for 2 h. The membrane containing the protein of interest was cut out according to the molecular weight and then blocked with PBS containing 5% skim milk at room temperature for 2 hours; anti-α-synuclein antibody was added at 1:1000 and incubated at room temperature for 2 h; the membrane was washed 3 times with 0.1% PBST, 5 min for each time; IR-conjugated goat anti-mouse/rabbit secondary antibody was added at 1:15000, incubated at room temperature in dark for 1 h; the membrane was washed 3 times with 0.1% PBST, 10 min for each time. Then the blots were imaged in a IR detection system. The results were shown in FIG. 12.

It can be seen that the ratio of soluble α-synuclein to α-tubulin in the brain of WT mice was 0.19; the ratio of soluble α-synuclein to α-tubulin in the brain of PD transgenic mice injected with ZR was 1.44; the ratio of soluble α-synuclein to α-tubulin in the brain of PD transgenic mice injected with PBS was 1.84; statistical analyses showed that the level of soluble α-synuclein in the brain of the PD transgenic mice injected with ZR was significantly lower than that in mice of PD control group.

Example 13 ZR Polypeptide Improved Motor Coordination of HD Transgenic Mice

Intracerebroventricular injection: 12-month-old HD transgenic mice were randomly divided into ZR-injected (HD+ZR) group and PBS-injected group, with 8 mice per group. Their WT littermates of the same age were used as control (WT). All the mice were treated as follows:

Mice were fasted for 12 hours before intracerebral injection and allowed to drink water ad-libitum. The mice were injected in the same manner as in example 6 and subjected to rotarod test.

Figure 13A:
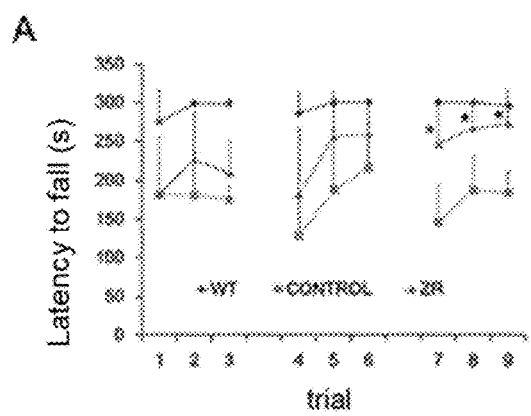
FIG. 13(A) shows the duration that HD transgenic mice stayed on rotarod, and FIG. 13 (B) shows the average latency of rotarod in 9 trails.
Figure 13B:
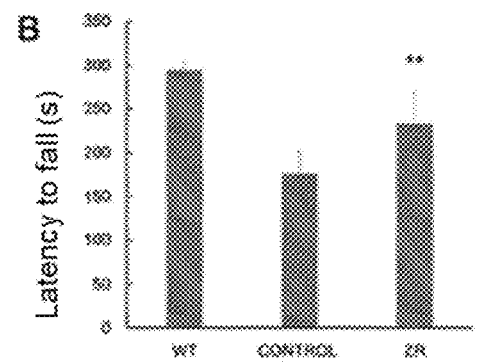

Rotarod test: the rotarod test was conducted for 3 consecutive days, and each day consisted of two phases: the training phase and the testing phase. Training phase: the rotation speed of the rotarod was at 4 rpm/min; mice were trained on the rotarod for 5 minutes and then placed back into cage; 1 h later, they were subjected to testing phase. Testing phase: the rotation speed of the rotarod was accelerated from standstill to 40 rpm/min within 5 minutes; the duration of mice on the rotarod was recorded, and if a mouse did not fall off, the duration was recorded as 300 s. The test was performed 3 times per day, with an interval of 30 minutes every time. Statistical analyses were performed on each group of mice for the durations thereof on rotarod in a total of 9 trials within 3 days. The results were shown in FIGS. 13(A)-(B): the latency of WT mice, HD control mice, and ZR-treated HD mice on rotarod were 295 s, 176.72 s, and 233.64 s, respectively.

Statistical analyses showed that HD mice injected with ZR had a significantly longer duration on rotarod than HD control mice.

Example 14 ZR Polypeptide Reduced HTT Level in the Brain of HD Transgenic Mice

Western blot method was performed to examine the effect of ZR on HTT level in the brain of HD transgenic mice.

Mice of ZR-injected (HD+ZR) group, PBS-injected group and WT group were subjected to heart perfusion, and the brains were harvested and weighed. The brain tissues were added, at a ratio of 1:5 (V/W), to RIPA lysate containing 1× protease inhibitor, homogenized on ice for 5 min, left for 20 min, and then centrifuged at 12000 rpm at 4° C. for 5 min, and the supernatant was collected.

Protein samples were prepared by mixing LDS buffer, reducing agent and a certain amount of soluble protein components thoroughly in a total volume of 10 μL, placed in a metal bath at 70° C. for 10 min, and then centrifuged at 12,000 rpm at room temperature for 5 min 3-8% Tris-acetate NuPAGE gel was used, with 10 μl of sample loaded per well, and electrophoresed at 150 V for 80 min. Then the proteins were transferred onto a membrane at 300 mA for 2 hours. The NC membrane containing the protein of interest was cut out according to the molecular weight and blocked with PBS containing 5% skim milk at room temperature for 2 hours; anti-HTT antibody 2166 (1:1000) or α-tubulin antibody (1:1000) was added and incubated for at room temperature for 2 h; the membrane was washed 3 times with 0.1% PBST, 5 min for each time; IR-stained goat anti-mouse/rabbit secondary antibody was added at 1:15000, incubated at room temperature in dark for 1 h; the membrane was washed 3 times with 0.1% PBST, 10 min for each time. Then, the optical density of the light-emitting strip on the membrane was detected by an infrared laser imaging system, and the results were shown in FIG. 14.

Figure 14:
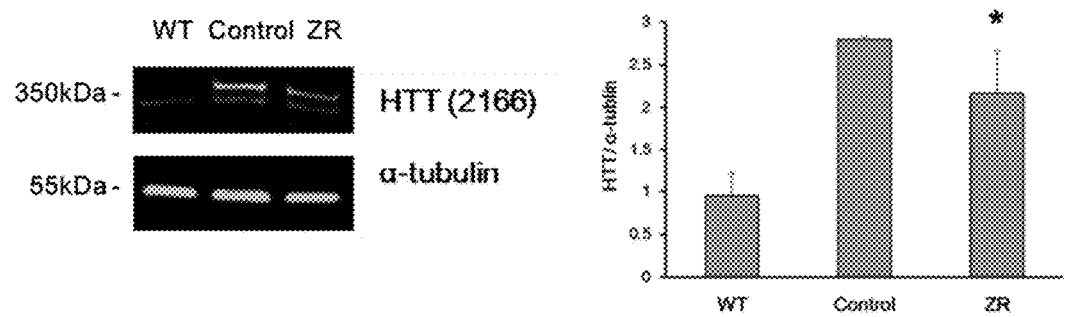
FIG. 14 shows that the polypeptide of the present invention reduced HTT protein level in the brain of HD transgenic mice.

FIG. 14 shows that the ratio of soluble HTT/α-tubulin in the brain of WT mice was 0.955; the ratio of soluble HTT/α-tubulin in the brain of HD transgenic mice injected with ZR was 2.17; the ratio of soluble HTT/α-tubulin in the brain of HD transgenic mice injected with PBS was 2.79; statistical analyses showed that the level of soluble HTT in the brain of HD transgenic mice injected with ZR was significantly lower than that in HD control mice.

The applicant states that the present invention describes the process of the present invention through the above embodiments, however, the present invention is not limited to the above process steps, that is to say, it doesn't mean that the present invention must rely on the above process steps to implement. It should be apparent to those skilled in the art that any improvement of the present invention, the equivalent replacement of the raw materials used in the present invention and the addition of auxiliary components, the selection of specific methods, etc., all fall within the protection scope and the disclosure scope of the present invention.

The invention claimed is:

1. An oligopeptide binding to a plurality of amyloid monomers and aggregates, wherein said oligopeptide consists of the amino acid sequence selected from SEQ ID NOs: 2, 4-6, 8, and 10.

2. A DNA fragment, comprising a nucleotide sequence encoding the oligopeptide according to claim 1.

3. A recombinant vector, comprising at least one copy of the DNA fragment according to claim 2.

4. An inhibitor of amyloid cytotoxicity, comprising the oligopeptide according to claim 1.

5. An inhibitor of amyloid aggregation, comprising the oligopeptide according to claim 1.

6. An accelerator for the clearance of Aβ by cells, comprising the oligopeptide according to claim 1.

7. The inhibitor of amyloid cytotoxicity according to claim 4, which is an inhibitor of the cytotoxicity of Aβ, amylin, insulin and lysozyme on cells.

8. The inhibitor of amyloid cytotoxicity according to claim 4, wherein the cells are SH-SY5Y neuroblastoma cells.

9. The inhibitor of amyloid aggregation according to claim 5, which is an inhibitor of the aggregation of Aβ and lysozyme.

10. The promoter for the clearance of Aβ by cells according to claim 6, wherein the cells are microglia.

11. The promoter for the clearance of Aβ by cells according to claim 6, wherein the Aβ is Aβ342.

12. The promoter for the clearance of Aβ by cells according to claim 6, wherein the cells are BV-2 cells.

* * * * *

SEQUENCE LISTING

```
<160> NUMBER OF SEQ ID NOS: 13

<210> SEQ ID NO 1
<211> LENGTH: 7
<212> TYPE: PRT
<213> ORGANISM: Artifical sequence
<220> FEATURE:
<221> NAME/KEY: misc_feature
<222> LOCATION: (2)..(2)
<223> OTHER INFORMATION: Xaa can be any naturally occurring amino acid
<220> FEATURE:
```

```
<221> NAME/KEY: misc_feature
<222> LOCATION: (4)..(4)
<223> OTHER INFORMATION: Xaa can be any naturally occurring amino acid

<400> SEQUENCE: 1

Ser Xaa Phe Xaa Asn Lys Arg
1               5

<210> SEQ ID NO 2
<211> LENGTH: 7
<212> TYPE: PRT
<213> ORGANISM: Artifical sequence
<220> FEATURE:
<223> OTHER INFORMATION: synthetic peptide

<400> SEQUENCE: 2

Ser Phe Phe Asn Asn Lys Arg
1               5

<210> SEQ ID NO 3
<211> LENGTH: 6
<212> TYPE: PRT
<213> ORGANISM: Artifical sequence
<220> FEATURE:
<223> OTHER INFORMATION: synthetic peptide

<400> SEQUENCE: 3

Ser Phe Phe Asn Lys Arg
1               5

<210> SEQ ID NO 4
<211> LENGTH: 7
<212> TYPE: PRT
<213> ORGANISM: Artifical sequence
<220> FEATURE:
<223> OTHER INFORMATION: synthetic peptide

<400> SEQUENCE: 4

Ser Ala Phe Gln Asn Lys Arg
1               5

<210> SEQ ID NO 5
<211> LENGTH: 8
<212> TYPE: PRT
<213> ORGANISM: Artifical sequence
<220> FEATURE:
<223> OTHER INFORMATION: synthetic peptide

<400> SEQUENCE: 5

Ser Phe Phe Asn Asn Asn Lys Arg
1               5

<210> SEQ ID NO 6
<211> LENGTH: 8
<212> TYPE: PRT
<213> ORGANISM: Artifical sequence
<220> FEATURE:
<223> OTHER INFORMATION: synthetic peptide

<400> SEQUENCE: 6

Ser Phe Phe Asn Asn Lys Arg Lys
1               5

<210> SEQ ID NO 7
<211> LENGTH: 7
<212> TYPE: PRT
<213> ORGANISM: Artifical sequence
```

```
<220> FEATURE:
<223> OTHER INFORMATION: synthetic peptide

<400> SEQUENCE: 7

Ala Phe Phe Asn Asn Lys Arg
1               5

<210> SEQ ID NO 8
<211> LENGTH: 7
<212> TYPE: PRT
<213> ORGANISM: Artifical sequence
<220> FEATURE:
<223> OTHER INFORMATION: synthetic peptide

<400> SEQUENCE: 8

Ser Ala Phe Asn Asn Lys Arg
1               5

<210> SEQ ID NO 9
<211> LENGTH: 7
<212> TYPE: PRT
<213> ORGANISM: Artifical sequence
<220> FEATURE:
<223> OTHER INFORMATION: synthetic peptide

<400> SEQUENCE: 9

Ser Phe Ala Asn Asn Lys Arg
1               5

<210> SEQ ID NO 10
<211> LENGTH: 7
<212> TYPE: PRT
<213> ORGANISM: Artifical sequence
<220> FEATURE:
<223> OTHER INFORMATION: synthetic peptide

<400> SEQUENCE: 10

Ser Phe Phe Ala Asn Lys Arg
1               5

<210> SEQ ID NO 11
<211> LENGTH: 7
<212> TYPE: PRT
<213> ORGANISM: Artifical sequence
<220> FEATURE:
<223> OTHER INFORMATION: synthetic peptide

<400> SEQUENCE: 11

Ser Phe Phe Asn Ala Lys Arg
1               5

<210> SEQ ID NO 12
<211> LENGTH: 7
<212> TYPE: PRT
<213> ORGANISM: Artifical sequence
<220> FEATURE:
<223> OTHER INFORMATION: synthetic peptide

<400> SEQUENCE: 12

Ser Phe Phe Asn Asn Ala Arg
1               5

<210> SEQ ID NO 13
<211> LENGTH: 7
<212> TYPE: PRT
<213> ORGANISM: Artifical sequence
<220> FEATURE:
```

```
<223> OTHER INFORMATION: synthetic peptide

<400> SEQUENCE: 13

Ser Phe Phe Asn Asn Lys Ala
1               5
```